United States Patent
Bassler et al.

(10) Patent No.: US 7,701,580 B2
(45) Date of Patent: Apr. 20, 2010

(54) TRANSMITTING/REFLECTING EMANATING LIGHT WITH TIME VARIATION

(75) Inventors: Michael Bassler, Menlo Park, CA (US); Markus Beck, Palo Alto, CA (US); Peter Kiesel, Palo Alto, CA (US); Alex Hegyi, Ann Arbor, MI (US); Tobias Buergel, Braunschweig (DE); Noble M. Johnson, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 0 days.

(21) Appl. No.: 12/024,490

(22) Filed: Feb. 1, 2008

(65) Prior Publication Data

US 2009/0195773 A1    Aug. 6, 2009

(51) Int. Cl.
   *G01N 21/25*   (2006.01)
(52) U.S. Cl. .................................................... 356/419
(58) Field of Classification Search ................ 356/419, 356/410, 73, 318, 343; 359/890
   See application file for complete search history.

(56) References Cited

U.S. PATENT DOCUMENTS

| | | | |
|---|---|---|---|
| 4,081,277 | A | 3/1978 | Brault et al. |
| 4,764,670 | A | 8/1988 | Pace et al. |
| 5,370,842 | A | 12/1994 | Miyazaki et al. |
| 5,445,934 | A | 8/1995 | Fodor et al. |
| 5,682,038 | A | 10/1997 | Hoffman |
| 5,760,900 | A * | 6/1998 | Ito et al. ................ 356/338 |
| 5,798,222 | A | 8/1998 | Goix |
| 5,872,655 | A | 2/1999 | Seddon et al. |

(Continued)

FOREIGN PATENT DOCUMENTS

WO    WO 95/20144    7/1995

(Continued)

OTHER PUBLICATIONS

Adams, M.L., Enzelberger, M., Quake, S., and Scherer, A., "Microfluidic integration on detector arrays for absorption and fluorescence micro-spectrometers", Sensors and Actuators, 2003, pp. 25-31.

(Continued)

*Primary Examiner*—Gregory J Toatley, Jr.
*Assistant Examiner*—Abdullahi Nur
(74) *Attorney, Agent, or Firm*—Leading-Edge Law Group, PLC; Mark W. Hrozenchik

(57) ABSTRACT

A filter arrangement can transmit and/or reflect light emanating from a moving object so that the emanating light has time variation, and the time variation can include information about the object, such as its type. For example, emanating light from segments of a path can be transmitted/reflected through positions of a filter assembly, and the transmission functions of the positions can be sufficiently different that time variation occurs in the emanating light between segments. Or emanating light from a segment can be transmitted/reflected through a filter component in which simpler transmission functions are superimposed, so that time variation occurs in the emanating light in accordance with superposition of two simpler non-uniform transmission functions. Many filter arrangements could be used, e.g. the filter component could include the filter assembly, which can have one of the simpler non-uniform transmission functions. Time-varying waveforms from sensing results can be compared to obtain spectral differences.

24 Claims, 21 Drawing Sheets

U.S. PATENT DOCUMENTS

| | | | |
|---|---|---|---|
| 6,040,578 | A | 3/2000 | Malin et al. |
| 6,091,502 | A | 7/2000 | Weigl et al. |
| 6,429,022 | B1 | 8/2002 | Kunz et al. |
| 6,558,945 | B1 | 5/2003 | Kao |
| 6,697,542 | B2 | 2/2004 | Platzman et al. |
| 6,816,257 | B2 | 11/2004 | Goix |
| 6,865,198 | B2 | 3/2005 | Taubman |
| 6,867,420 | B2 | 3/2005 | Mathies et al. |
| 6,906,792 | B2 | 6/2005 | Ortyn et al. |
| 7,034,933 | B2 | 4/2006 | Walker et al. |
| 7,248,361 | B2 | 7/2007 | Kiesel et al. |
| 7,268,868 | B2 | 9/2007 | Kiesel et al. |
| 7,274,011 | B2 | 9/2007 | Tennant et al. |
| 7,291,824 | B2 | 11/2007 | Kiesel et al. |
| 7,315,667 | B2 | 1/2008 | Schmidt et al. |
| 7,440,101 | B2 | 10/2008 | Auer et al. |
| 7,471,399 | B2 | 12/2008 | Kiesel et al. |
| 7,479,625 | B2 | 1/2009 | Kiesel et al. |
| 7,502,123 | B2 | 3/2009 | Schmidt et al. |
| 7,545,513 | B2 | 6/2009 | Kiesel et al. |
| 7,547,904 | B2 | 6/2009 | Schmidt et al. |
| 7,554,673 | B2 | 6/2009 | Kiesel et al. |
| 2002/0155485 | A1 | 10/2002 | Kao |
| 2003/0235924 | A1 | 12/2003 | Adams et al. |
| 2004/0038386 | A1 | 2/2004 | Zesch et al. |
| 2004/0067167 | A1 | 4/2004 | Zhang et al. |
| 2005/0128479 | A1 | 6/2005 | Gilbert et al. |
| 2005/0162648 | A1 | 7/2005 | Auer et al. |
| 2006/0274313 | A1 | 12/2006 | Gilbert et al. |
| 2007/0046301 | A1 | 3/2007 | Kasapi |
| 2007/0070347 | A1 | 3/2007 | Scherer et al. |
| 2007/0145249 | A1 | 6/2007 | Kiesel et al. |
| 2007/0146704 | A1 | 6/2007 | Schmidt et al. |
| 2007/0147189 | A1 | 6/2007 | Schmidt et al. |
| 2007/0147728 | A1 | 6/2007 | Schmidt et al. |
| 2007/0172969 | A1 | 7/2007 | Wong et al. |
| 2008/0013092 | A1 | 1/2008 | Maltezos et al. |
| 2008/0013877 | A1 | 1/2008 | Schmidt et al. |
| 2008/0181827 | A1 | 7/2008 | Bassler et al. |
| 2008/0183418 | A1 | 7/2008 | Bassler et al. |
| 2008/0186488 | A1 | 8/2008 | Kiesel et al. |
| 2008/0186492 | A1 | 8/2008 | Kiesel et al. |
| 2008/0186504 | A1 | 8/2008 | Kiesel et al. |
| 2008/0299327 | A1 | 12/2008 | Salleo et al. |
| 2009/0190121 | A1 | 7/2009 | Hagyi et al. |
| 2009/0194705 | A1 | 8/2009 | Kiesel et al. |
| 2009/0195852 | A1 | 8/2009 | Bassler et al. |

FOREIGN PATENT DOCUMENTS

| | | | |
|---|---|---|---|
| WO | WO 00/62050 A1 | 10/2000 | |

OTHER PUBLICATIONS

Shapiro, H. M., Practical Flow Cytometry, Fourth Edition, Wiley-Liss, 2003, Table of Contents and pp. 49-59, 124-183, 191-197, 345, and 364-366.

Hoffman, R. A., "Flow Cytometry: Instrumentation, Applications, Future Trends and Limitations", Springer Series on Fluorescence, vol. 6, 2008, pp. 307-342.

Office communication in U.S. Appl. No. 11/702,470, mailed Apr. 25, 2008, 22 pages, published in PAIR.

Amendment in U.S. Appl. No. 11/702,470, submitted Jul. 25, 2008, 21 pages, published in PAIR.

Office communication in U.S. Appl. No. 11/702,470, mailed Oct. 31, 2008, 22 pages, published in PAIR.

Amendment in U.S. Appl. No. 11/702,470, submitted Jan. 30, 2009, 22 pages, published in PAIR.

Notice of Allowance and Fee(s) Due in U.S. Appl. No. 11/702,470, mailed Apr. 24, 2009, 15 pages, published in PAIR.

Office communication in U.S. Appl. No. 12/023,436, mailed Dec. 23, 2008, 15 pages.

Amendment in U.S. Appl. No. 12/023,436, submitted Mar. 23, 2009, 22 pages.

Office communication in U.S. Appl. No. 12/022,485, mailed Jan. 16, 2009, 18 pages.

Amendment in U.S. Appl. No. 12/022,485, submitted Apr. 15, 2009, 30 pages.

Bassler, et al., U.S. Appl. No. 12/025,394, Feb. 4, 2008, 61 pages.

Bracewell, R. N., The Fourier Transform and Its Applications, Second Edition, McGraw-Hill, 1978, Table of Contents and pp. 24-50, 98-126, and 177-188.

Bassler, ., Schmidt, O, Kiesel, P., Johnson, N.M., "Class Identification of Bio-Molecules Based on Multi-Color Native Fluorescence Spectroscopy", International Journal of High Speed Electronics and Systems (IJHSES), vol. 17, Issue 4, 2007, pp. 671-680.

Bhatta, H., Goldys, E.M., and Learmonth, R., "Rapid Identification of Microorganisms by Intrinsic Fluorescence", Proc. of SPIE, vol. 5699, 2005, pp. 9-18.

"Flow Cytometry", printed from www.wellscenter.iupui.edu/MMIA on Jan. 29, 2008, 4 pages.

Office communication in U.S. Appl. No. 12/023,436, mailed Jun. 12, 2009, 20 pages, published in PAIR.

Amendment in U.S. Appl. No. 12/023,436, submitted Sep. 3, 2009, 29 pages, published in PAIR.

Office communication in U.S. Appl. No. 12/022,485, mailed Jul. 31, 2009, 5 pages, published in PAIR.

Response to Restriction Requirement in U.S. Appl. No. 12/022,485, submitted Aug. 27, 2009, 20 pages, published in PAIR.

Office communication in U.S. Appl. No. 12/025,394, mailed Jan. 22, 2010, 19 pages, published in PAIR.

Office communication in U.S. Appl. No. 11/698,409, mailed Nov. 17, 2009, 18 pages, published in PAIR.

* cited by examiner

FIG. 9
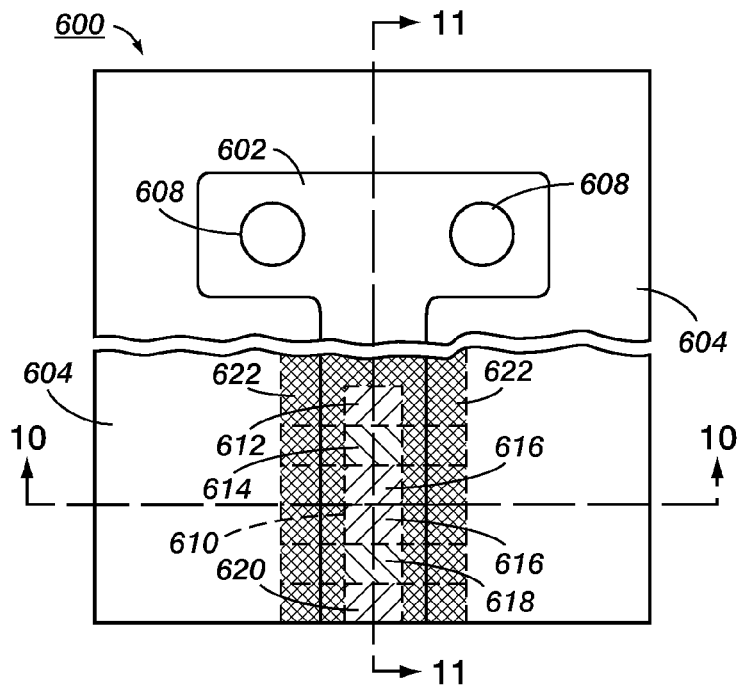
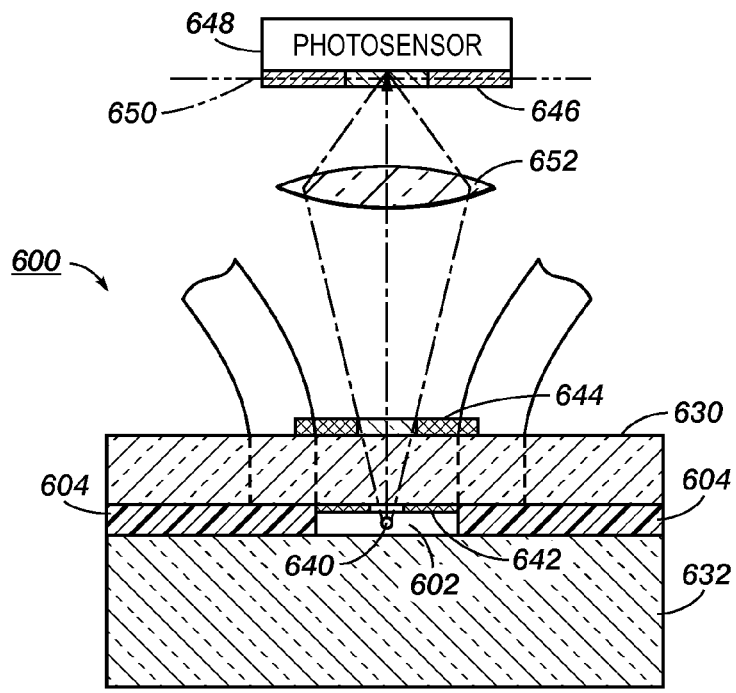
FIG. 10

TRANSMITTING/REFLECTING EMANATING LIGHT WITH TIME VARIATION

The following applications, each of which is hereby incorporated by reference in its entirety, might be regarded as related to this application: "Additive Printed Mask Process and Structures Produced Thereby", U.S. patent application Ser. No. 10/536,102, now published as U.S. Patent Publication No. 2007/0172969; "Sensing Photon Energies Emanating from Channels or Moving Objects", U.S. patent application Ser. No. 11/315,386, now published as U.S. Patent Publication No. 2007/0146704; "Sensing Photon Energies of Optical Signals", U.S. patent application Ser. No. 11/315,926, now published as U.S. Patent Publication No. 2007/0147189; "Sensing Photons from Objects in Channels", U.S. patent application Ser. No. 11/315,992, now published as U.S. Patent Publication No. 2007/0145249; "Obtaining Analyte Information", U.S. patent application Ser. No. 11/316,303, now published as U.S. Patent Publication No. 2007/0148760; "Providing Light to Channels or Portions", U.S. patent application Ser. No. 11/316,660, now published as U.S. Patent Publication No. 2007/0147728; "Method and System for Evaluation of Signals Received from Spatially Modulated Excitation and Emission to Accurately Determine Particle Positions and Distances", U.S. patent application Ser. No. 11/698,338; "Method and System Implementing Spatially Modulated Excitation or Emission for Particle Characterization with Enhanced Sensitivity", U.S. patent application Ser. No. 11/698,409; "Obtaining Information From Optical Cavity Output Light", U.S. patent application Ser. No. 11/702,249; "Photosensing Optical Cavity Output Light", U.S. patent application Ser. No. 11/702,250; "Distinguishing Objects", U.S. patent application Ser. No. 11/702,328; "Encoding Optical Cavity Output Light", U.S. patent application Ser. No. 11/702,363; "Moving Analytes and Photosensors", U.S. patent application Ser. No. 11/702,470; "Surface Energy Control Methods for Color Filter Printing", U.S. patent application Ser. No. 11/755,717; "Producing Sandwich Waveguides", U.S. patent application Ser. No. 11/777,661; "Producing Fluidic Waveguides", U.S. patent application Ser. No. 11/777,712; "Obtaining Information from Time Variation of Sensing Results", U.S. patent application Ser. No. 12/022,485; and "Providing Time Variation in Emanating Light", U.S. patent application Ser. No. 12/023,436.

BACKGROUND OF THE INVENTION

The present invention relates generally to techniques that transmit and/or reflect light emanating from objects. More specifically, techniques can use filter arrangements to transmit and/or reflect such light with time variation, such as where the objects are moving relative to the filter arrangements.

Various techniques have been proposed for using light emanating from objects. For example, U.S. Patent Application Publication No. 2007/0145249 describes a fluidic structure with a channel along which is a series of sensing components to obtain information about objects traveling within the channel, such as droplets or other objects carried by fluid. A sensing component includes a set of cells that photosense a range of photon energies that emanate from objects. A processor can receive information about objects from the sensing components and use it to obtain spectral information. Similar techniques are described, for example, in U.S. Patent Application Publication Nos. 2007/016704, 2007/0147189, and 2007/0147728.

Also, various flow cytometry techniques have been proposed.

It would be advantageous to have improved techniques for using light emanating from objects, including improved techniques for transmitting and/or reflecting such light with time variation.

SUMMARY OF THE INVENTION

The invention provides various exemplary embodiments, including methods and apparatus. In general, the embodiments involve transmitting and/or reflecting emanating light through filter arrangements to obtain time variation.

These and other features and advantages of exemplary embodiments of the invention are described below with reference to the accompanying drawings.

BRIEF DESCRIPTION OF THE DRAWINGS

FIG. 9 is a top view of an article that can include a filter arrangement and that can be included in an encoding component as in FIG. 2.

FIG. 10 is a cross-sectional view of an implementation of an article similar to that in FIG. 9, taken along the line 10-10.

DETAILED DESCRIPTION

Figure 1:
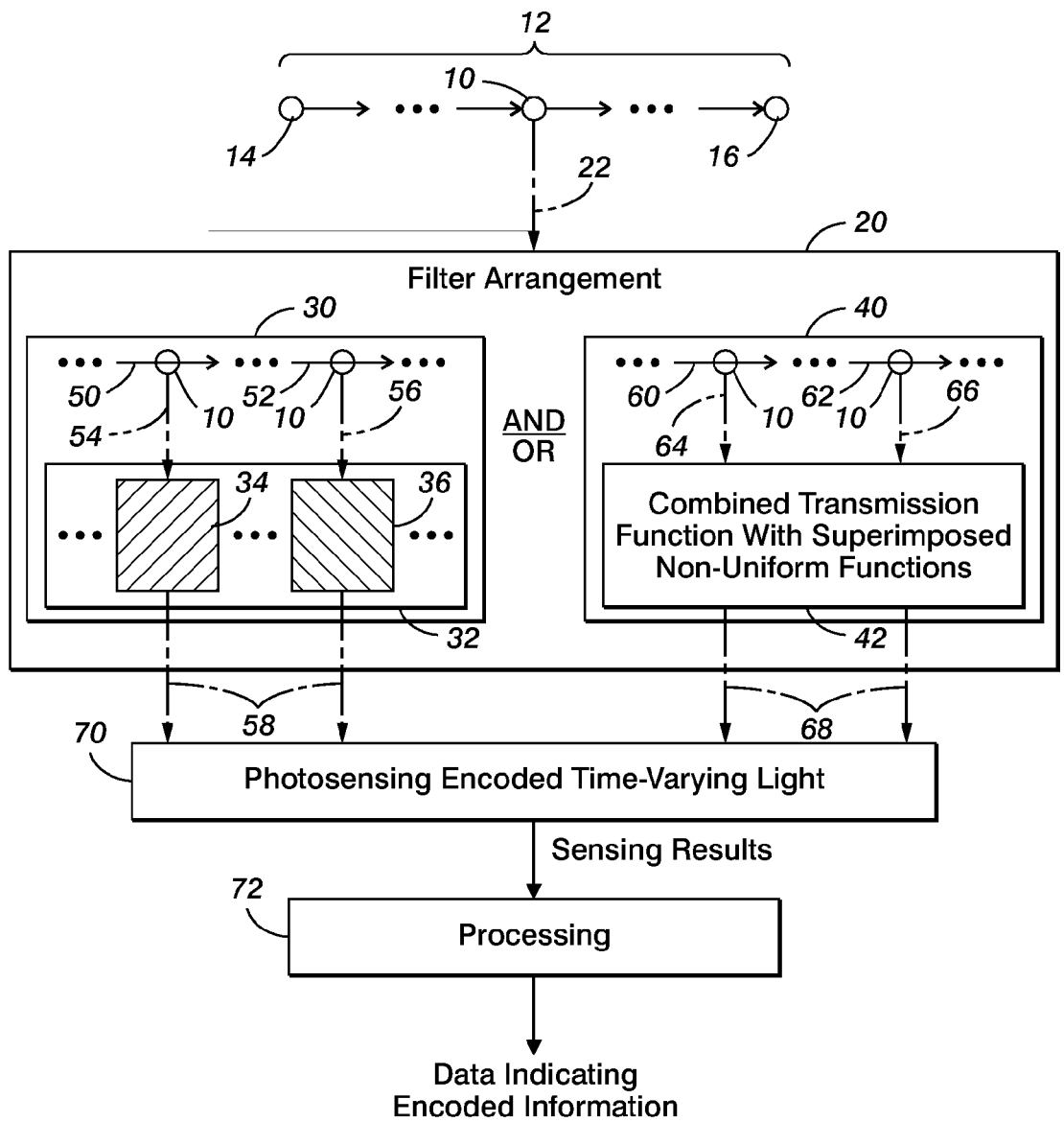
FIG. 1 is a schematic diagram showing features of techniques in which a filter arrangement transmits and/or reflects light emanating from an object with time variation.

In the following detailed description, numeric values and ranges are provided for various aspects of the implementations described. These values and ranges are to be treated as examples only, and are not intended to limit the scope of the claims. In addition, a number of materials are identified as suitable for various facets of the implementations. These materials are to be treated as exemplary, and are not intended to limit the scope of the claims.

"Light" refers herein to electromagnetic radiation of any wavelength or frequency; unless otherwise indicated, a specific value for light wavelength or frequency is that of light propagating through vacuum. Light that can include information is sometimes referred to herein as an "optical signal".

The term "sensing" is used herein in the most generic sense of obtaining information from a physical stimulus; sensing therefore includes actions such as detecting, measuring, and so forth. A "sensor" is a device that performs sensing. Data or other signals that indicate or include results of sensing are sometimes referred to herein as "sensing results".

"Photosensing" is sensing of light. A "photosensor" is accordingly an electronic device that performs photosensing. More specifically, if optical signals include information, a photosensor that receives the optical signals may be able to sense the information and provide sensing results that indicate or include the information. A surface at which photosensing occurs is referred to herein as a "photosensitive surface".

The various exemplary implementations described below address problems that arise in obtaining information about a moving object such as a biological cell, a virus, a molecule, or a submolecular complex, such as in flow cytometry. Flow cytometry has become an indispensable tool in clinical diagnostics, such as in diagnosing cancer, AIDS, and infectious diseases during outbreaks, and also in microbiology and other areas. The cost and size of existing cytometers preclude their use in field clinics, water monitoring, agriculture/veterinary diagnostics, and rapidly deployable biothreat detection.

A number of commercially available flow cytometers use multiple excitation sources, each focused on a well-defined location or region separate from the others. Light emitted from each source's region is typically analyzed with a series of beam splitters, filters, and photomultiplier tubes (PMTs) in order to detect and distinguish differently stained cells or cells that concurrently carry multiple dyes. Cells are typically stained in solution with different dyes prior to insertion into a cytometer, and the measurement takes place in a fluidic channel in which cells traverse a detection region, typically at a speed of up to several meters per second. In the detection region, focused laser light (typically with an elliptical focus of 80 μm×40 μm) excites the dyes on the cells. The resulting fluorescent light can be collected by a microscope lens, sorted by band pass filters, and detected by PMTs or avalanche photodiodes (APDs). For each spot excitation, a respective set of filters and detectors is needed, which is costly and leads to bulky devices with strict requirements necessary to maintain optical alignment. Since the detection region is small and objects traverse it rapidly (typical dwell times are around 10 μsec), such flow cytometers have serious signal-to-noise (S/N) ratio issues for weakly fluorescing cells. These issues become more acute if multiple targets must be characterized and distinguished in some way, such as by counting.

A major cost in flow cytometry applied in clinical diagnostics is cost of reagents (e.g. antibodies and conjugated dyes). There are two ways to reduce the amount of consumables: First, one can reduce the required amount of analyte, e.g. by employing microfluidic techniques; and second, one can reduce the amount of consumable per analyte volume. Reducing amounts used would, however, reduce fluorescent intensity. It would be valuable to be able to overcome this constraint with a cost-effective and reliable technique to detect and distinguish weakly emitting cells.

Previous proposals to address these problems have involved spatially modulated single-color excitation to improve S/N ratios and to shift the detection limit toward weaker emitting cells. Spatial resolution can be maintained or improved in comparison with previous flow cytometry techniques, because fluorescing light is spatially modulated over a comparably large detection region; this is helpful because spatial resolution affects maximum detection or count rate of a device. But single-color techniques are limited, whether excitation is performed in a black/white approach or with a single-color interference pattern from a light source. Also, single-color techniques can encounter problems with wavelength sensitivity and bleaching of dyes. Because of low wavelength sensitivity, many flow cytometers with filter-PMT combinations are also constrained to use dyes with substantially different fluorescence wavelengths.

In addressing such problems, some exemplary implementations described below employ filter arrangements that transmit or reflect emanating light with one or both of two techniques: A filter assembly is used that provides different transmission functions in different segments of an object's path and/or a filter component is used that has a combined transmission function in which a set of simpler non-uniform transmission functions are superimposed. Such techniques make it possible to provide several different transmission functions in sequence within a relatively short part of an object's path, so that the object's emanating light is relatively constant across the different transmission functions. These techniques also allow much greater variation in filter arrangements than would be possible with binary, black/white masks or single color masks. In addition, these techniques can be implemented to maintain higher spatial resolution and to allow higher photon flux on a photosensor. Time variation of emanating light resulting from such filters may provide sufficient information to make spectral characterization of particles feasible. Use of multiple colors may be compatible with particle identification based on native fluorescence; in particular, patterned filter arrangements allow for detection of differences in emission spectra and even the very small differences that occur in native fluorescence spectra might be detectable. It may also enable advanced color monitoring in printing applications by detecting even small differences in the reflection spectra of color spots while they are moving past interdigitated or otherwise patchworked or patterned filter arrangements.

The term "photon" refers herein to a quantum of light, and the term "photon energy" refers herein to the energy of a photon. Light can be described as having a "photon energy distribution" or, more commonly, a "spectrum", meaning the combination of photon energies that are included in the light; highly monochromatic light, for example, has a photon energy distribution or spectrum with one peak energy value.

Light can also be described as provided by a "light source," which, unless otherwise specified, refers herein to any device, component, or structure that can provide light of the type described; examples of light sources relevant to the below-described implementations include various kinds of pulsed and unpulsed lasers and laser structures, laser diodes (LDs), light emitting diodes (LEDs), superluminescent LEDs (SLEDs), resonant cavity LEDs, sources of broadband light that is spectrally filtered such as with a monochromator, and so forth.

To "propagate" light through a region or structure is to transmit or otherwise cause the light to propagate through the region or structure. The light may be referred to as "propagated light" or "propagating light".

Propagating light can often be usefully characterized by direction and speed of propagation, with direction typically illustrated by one or more rays and with speed typically being described relative to the constant c, also referred to as the speed of light in vacuum. Where the speed of light in a medium M is a constant $c_M$ less than c, then M has an index of refraction $n_M = c/c_M$.

Where light changes direction in a way that can be illustrated or approximated as a vertex between an incoming ray and an outgoing ray that are both on one side of a surface, the change may be referred to as a "reflection"; similarly, to "reflect" light is to cause the light to change its direction of propagation approximately at such a surface, referred to herein as a "reflection surface". Similarly, where light changes direction in a way that can be illustrated or approximated as a vertex between an incoming ray and an outgoing ray that are on opposite sides of a surface between two media with different indices of refraction, the change may be referred to as a "refraction"; similarly, to "refract" light is to cause the light to change its direction of propagation approximately at such a surface, referred to herein as a "refraction surface". In many practical applications, both reflection and refraction occur at a surface, which may be referred to herein as a "partially reflecting surface".

Where light propagates at less than c, it may be useful to obtain an "optical distance" of propagation; for any segment of length d in which speed of propagation is constant $\epsilon^* c$, where $\epsilon = 1/n_{EFF} \leq 1$ and $n_{EFF}$ is an effective index of refraction for the segment, optical distance $D(\epsilon) = d/\epsilon$. An optical distance may be referred to herein as an "optical thickness", such as where light is propagating through a thickness of material.

A "range of photon energies" or an "energy range" is a range of energy values that photons can have. An energy range can be described, for example, as a range of wavelengths or a range of frequencies or, in appropriate cases, by the range's central wavelength or frequency and possibly also the range's width. A "subrange" of a range of photon energies is a part of the range, and can be similarly described.

In general, the upper and lower boundaries and widths of ranges and subranges are approximate. To provide output photons or to photosense quantity of photons "throughout", "within", or "in" a range or subrange means to provide photons or to obtain information about quantity of photons that are predominantly within the range or subrange. In typical cases, between 60-90% of the provided photons or sensed quantity of photons have energies within the range or subrange, but the percentage could be lower or higher. In some applications, 90% or even 95% or more of the provided photons or sensed quantity of photons have energies within the range or subrange.

The term "electrical signal" is used herein to encompass any signal that transfers information from one position or region to another in an electrical, electronic, electromagnetic, or magnetic form. Electrical signals may be conducted from one position or region to another by electrical or magnetic conductors, but the broad scope of electrical signals also includes light and other electromagnetic forms of signals and other signals transferred through non-conductive regions due to electrical, electronic, electromagnetic, or magnetic effects. In general, the broad category of electrical signals includes both "analog" and "digital" signals: An "analog" electrical signal includes information in the form of a continuously variable physical quantity, such as voltage; a "digital" electrical signal, in contrast, includes information in the form of discrete values of a physical characteristic, which could also be, for example, voltage.

Some implementations of filter arrangements described herein employ structures with one or more dimensions smaller than 1 mm, and various techniques have been proposed for producing such structures. In particular, some techniques for producing such structures are referred to as "microfabrication." Examples of microfabrication include various techniques for depositing materials such as growth of epitaxial material, sputter deposition, evaporation techniques, plating techniques, spin coating, printing, and other such techniques; techniques for patterning materials, such as etching or otherwise removing exposed regions of thin films through a photolithographically patterned resist layer or other patterned layer; techniques for polishing, planarizing, or otherwise modifying exposed surfaces of materials; and so forth.

In the implementations described below, structures, systems, or parts or components of structures or systems may sometimes be referred to as "attached" to each other or to other structures, systems, parts, or components or visa versa, and operations are performed that "attach" structures, systems, or parts or components of structures or systems to each other or to other things or visa versa; the terms "attached", "attach", and related terms refer to any type of connecting that could be performed in the context. One type of attaching is "mounting", which occurs when a first part or component is attached to a second part or component that functions as a support for the first. In contrast, the more generic term "connecting" includes not only "attaching" and "mounting", but also making other types of connections such as electrical connections between or among devices or components of circuitry. A combination of one or more parts connected in any way is sometimes referred to herein as a "structure".

Some of the structures, elements, and components described herein are supported on a "support structure" or "support surface", which terms are used herein to mean a structure or a structure's surface that can support other structures. More specifically, a support structure could be a "substrate", used herein to mean a support structure on a surface of which other structures can be formed or attached by microfabrication or similar processes.

The surface of a substrate or other support surface is treated herein as providing a directional orientation as follows: A direction away from the surface is "up", "over", or "above", while a direction toward the surface is "down", "under", or "below". The terms "upper" and "top" are typically applied to structures, components, or surfaces disposed away from the surface, while "lower" or "underlying" are applied to structures, components, or surfaces disposed toward the surface. In general, it should be understood that the above directional orientation is arbitrary and only for ease of description, and that a support structure or substrate may have any appropriate orientation.

A structure may be described by its operation, such as a "support structure" that can operate as a support as described above; other examples are defined below. In addition, a structure may be characterized by the nature of its parts or the way in which they are connected; for example, a "layered structure" is a structure that includes one or more layers, and the terms "partial structure" and "substructure" refer to structures that are in turn parts of other structures.

Unless the context indicates otherwise, the terms "circuitry" and "circuit" are used herein to refer to structures in which one or more electronic components have sufficient electrical connections to operate together or in a related manner. In some instances, an item of circuitry can include more than one circuit. An item of circuitry that includes a "processor" may sometimes be analyzed into "hardware" and "software" components; in this context, "software" refers to stored or transmitted data that controls operation of the processor or that is accessed by the processor while operating, and "hardware" refers to components that store, transmit, and operate on the data. The distinction between "software" and "hardware" is not always clear-cut, however, because some components share characteristics of both; also, a given software component can often be replaced by an equivalent hardware component without significantly changing operation of circuitry, and a given hardware component can similarly be replaced by equivalent processor operations controlled by software.

Circuitry can be described based on its operation or other characteristics. For example, circuitry that performs control operations is sometimes referred to herein as "control circuitry" and circuitry that performs processing operations is sometimes referred to herein as "processing circuitry".

In general, sensors, processors, and other such items may be included in a system in which they are operated automatically or partially automatically. As used herein, the term "system" refers to a combination of two or more parts or components that can perform an operation together. A system may be characterized by its operation; for example, an "object distinguishing system" is a system that operates somehow to distinguish objects.

Within a system, device, or other article, components and parts may be referred to in a similar manner. One component of an object distinguishing system, for example, can be described as an "encoding component", in some cases referred to as an "encoding arrangement", in either case meaning that the component or arrangement operates to encode information; similarly, a system can include an "filter component", in some cases referred to as an "filter arrangement", in either case meaning that the component or arrangement operates to perform filtering, as explained in greater detail below; various other components are described below. In addition, a component or part may be identified by characteristics other than its operation.

In FIG. 1, object 10 is one of series 12 of objects 14 through 16 that travel along respective paths past filter arrangement 20. The term "path" is used herein in the general sense of a series of positions and/or configurations that a moving and/or varying object can have during its motion and/or variation. For generality, a part of a path is sometimes referred to herein as a "segment", which could encompass any continuous series of one or more positions and/or configurations within a path.

As object 10 travels past arrangement 20, light emanates from it, such as by emission, scattering (including, e.g. reflection), or transmission, and a portion of the emanating light is received by filter arrangement 20, as indicated by arrow 22. In general, the emanating light includes light within an application's range of photon energies, meaning that techniques as in FIG. 1 can be successfully used in a given application, e.g. flow cytometry, bio-chip readout, or any suitable kind of analyte detection, even though emanating light might also include photon energies that are outside the application's range and that might not interact with filter arrangement 20 in the same way as light in the application's range.

The term "object" is used herein in the general sense of any distinguishable thing about which information can be obtained by a sensor and included in its sensing results. In some implementations, sensors can obtain information about objects by receiving signals from them; for example, signals in the form of light can emanate from an object, whether through emission (e.g. radiation, fluorescence, incandescence, chemoluminescence, bioluminescence, other forms of luminescence, etc.), scattering (e.g. reflection, deflection, diffraction, refraction, etc.), or transmission, and can be sensed by a photosensor. The light "emanates from" or is simply "from" the object, and may be referred to herein as "emanating light". An object from which light is emanating may be referred to herein as a "light-emanating object". In other implementations, sensors can obtain information about objects in other ways, some of which are mentioned herein.

Examples of objects that could occur in implementations as described below include droplets, small volumes of fluid, single molecules, agglomerated molecules, molecule clusters, cells, viruses, bacteria, lengthy polymers such as DNA or protein chains, submolecular complexes such as tags on DNA or protein chains, microparticles, nanoparticles, beads or other small particles that can bind and carry specific chemicals or other analytes, emulsions, any such type of object in an array such as an array of sample wells, and a distinguishable region of a surface such as a small area of a sheet of paper or other image-bearing medium; a distinguishable region, could, for example, be a colored spot. A droplet or small volume of fluid may, for example, include atoms, molecules, or other particles that emit light spontaneously or in response to excitation; a particle could be a "fluorescent component" of a droplet, fluorescing in response to excitation. Or a droplet may include particles that absorb light incident on the droplet, so that the droplet does not reflect or otherwise scatter the absorbed light; in this case, a particle could be an "absorbent component" of a droplet. Or a droplet may include particles that scatter light incident on the droplet in a way that depends on photon energy, so that the droplet scatters the incident light correspondingly; in this case, a particle could be a "scattering component" of a droplet. An analyte (i.e. a chemical species being investigated) in a droplet or other object can act as a fluorescent, absorbent, or scattering component. Analyte that is otherwise homogeneously distributed, for example, can be localized by binding to carrier beads, resulting in a moving object that emanates light or provides other signals in a way that depends on the analyte.

With respect to a light-emanating object, the expressions "characteristic of an object" and "emanating light including information" have related meanings: The term "characteristic" refers to a trait, quality, or property of an object that can be measured and that persists with a given value or within a given range or other subset of possible values while light that "includes information about the characteristic" is emanating from the object. In appropriate implementations, characteristics of an object could include mass, volume, density, cross-section or other shape, chemical composition, position, speed, acceleration, direction of movement, spin axis, directional or angular velocity or momentum, net charge, charge polarity, absorption spectrum, emission spectrum, scattering spectrum, and so forth. Therefore, emanating light "includes" information about a characteristic of an object if information included in the emanating light indicates a value, range, or other measure of the characteristic. Similar terminology can apply to types of signals other than emanating light.

Emanating light or other types of signals can "include information" in many ways, some of which are described below in relation to specific implementations. Various criteria could be used to determine whether emanating light or another type of signal includes specified information, and such criteria can be referred to as "encoding criteria". Some encoding criteria, for example, involve comparison of magnitude of a signal with noise magnitude, e.g. signal-to-noise (S/N) ratios, because S/N ratio can affect whether specified information can be recovered from sensing results obtained by photosensing emanating light. Other types of encoding criteria could be used as appropriate. Where emanating light or another type of signal satisfies an appropriate encoding criterion for specified information, the light or signal may be said to "encode" the information.

Similarly, sensing results, whether from photosensing emanating light or from another type of sensing, can "include information" in many ways, and similar encoding criteria could be applied as with signals. Where sensing results indicate one or more time-varying waveforms, the sensing results can be referred to as having "encoded time variation".

The term "waveform" is used herein in the general sense of any set of values that varies over one or more dimensions, whether continuous or discrete, whether analog or digital, and whether measured or obtained in any other way; a "time-varying waveform" is a waveform that varies over a time dimension. Some of the time-varying waveforms described below in relation to exemplary implementations include intensity values, but the expression "time-varying waveforms" also encompasses other values that vary over time, including purely numerical values with no specified units or other physical significance. A "sensed time-varying waveform" is a time-varying waveform that is indicated by sensing results obtained over time. For example, if a photosensor provides sensed quantities that indicate intensity of received light, its sensing results could indicate a time-varying waveform indicating intensity sensed over time.

In a system in which sensing results, emanating light, or other signals can include information about characteristics of objects, an object "travels" or is caused "to travel" if the object has a succession of positions over time with respect to one or more parts or components of the system or one or more patterns or other features of the system's environment such that information about the object's traveling, e.g. about speed or other rate of displacement, can be included in the emanating light or other signals. An object that travels is sometimes also referred to herein as "moving" or as having "motion" or "movement", but an object's traveling may result from any appropriate motion of the object and/or motion of parts or components of the system or patterns or other features of its environment. In other words, motion of an object includes any relative movement between the object and parts or components of a system or patterns or features of the system's environment, such as an encoding or sensing component of the system or a pattern of excitation or of filtering or another environmental pattern or feature.

A moving object's path is treated herein as providing a directional orientation as follows: A direction parallel or approximately parallel to the path is sometimes referred to as a "longitudinal" or "lengthwise" direction, while a direction perpendicular or approximately perpendicular to the path is sometimes referred to as a "radial", "lateral", or "transverse" direction. The lengthwise direction in which the object is moving is sometimes referred to as "forward" or "downstream", while the opposite direction is sometimes referred to as "backward" or "upstream". A radial direction away from the path is "out" or "outward", while a radial direction toward the path is "in" or "inward". Light propagating toward the path may be referred to as "incoming" or "incident", while light propagating away from the path may be referred to as "outgoing". A component or arrangement of components is "along" the path if it is disposed near the path and has some extent in a longitudinal direction. A component or arrangement of components is "around" the path if, in a plane transverse to the path, it intersects multiple radial directions, at least two of which are separated by approximately 180 degrees of arc. A direction that similarly goes around the path is sometimes referred to herein as a "rotation" direction. In general, it should be understood that the above directional orientation is arbitrary and only for ease of description, and that a moving object's path may have any appropriate orientation.

Emanating light that includes information about an object's traveling is sometimes referred to herein as "motion-affected" light, as including "motion-dependent information", or as having "motion-dependent encoding". For example, an object could travel by being conveyed in fluid, such as liquid, gas, or aerosol, along a path in which it emanates light that is transmitted and/or reflected by a filter arrangement to include information about the object's motion, thus becoming motion-affected light; in such a case the object may be referred to as being "carried" by fluid. In another example, an object contained in or otherwise supported by a support structure could travel due to relative scanning movement between the support structure and a filter component or another component such as a photosensor, and it could emanate light that is transmitted and/or reflected so that it becomes motion-affected light.

The term "optical filter" or simply "filter" refers herein to a light-transmissive or light-reflective part or component that transmits and/or reflects light in accordance with a respective criterion, sometimes referred to herein as a filter's "type". For example, one general category of filters is "band pass filters", referring to types of filters that, across some application's range of photon energies, e.g. a range of wavelengths or frequencies such as the visible range, preferentially transmit and/or reflect light within a subrange, sometimes referred to as a "band"; a band pass filter's type can therefore be specified by specifying the band or subrange of photon energies in which it transmits and/or reflects. A "blocking filter", which does not transmit or reflect any light in an application's range, can be viewed as a band pass filter with a band of zero bandwidth, while a "transparent filter", which transmits and/or reflects all light in an application's range, can be viewed as a band pass filter with a band that includes the entire range.

Filters can be combined and configured in many different ways, and all such combinations and configurations of one or more filters are encompassed herein by the general term "filter arrangement". A filter arrangement can include, for example, one or more "filter components", one or more "filter assemblies", and/or one or more "filter elements"; while the term "filter component" is generic, referring to any component that operates as a filter, the terms "filter assembly" and "filter element" are related and therefore a bit more specific, in that a filter assembly is a filter component that includes one or more filter elements, while a filter element is a filter component that generally does not include other filter elements within it. In general, filter elements and filter assemblies are sometimes also referred to as "masks". Also, the terms "transmit" and "reflect" and related words, as used herein, include each other unless otherwise specified, and terms such as "transmit/reflect" or "transmitting/reflecting" encompass transmission without reflection, reflection without transmission, and concurrent transmission and reflection.

Filter elements of various kinds could be included in filter assemblies, filter components, filter arrangements, and other combinations and configurations of filters, in a wide variety of ways. Within a given configuration of filters, relationships between filters can be described in a number of ways. For example, light can pass through a "sequence" of filters, meaning that specified light passes through the filters in a sequence: If a "radial sequence" of filters is along a path, for example, emanating light can pass through each of the filters in the sequence, beginning with the first and, after passing through each preceding filter, passing through the following filter; of course, light that is blocked by a preceding filter in a radial sequence would not reach its following filter. If a "longitudinal sequence" of filters is along a path, on the other hand, light emanating at each of a sequence of segments of the path passes through a respective filter in the longitudinal sequence.

Several other categories of filters are described below in relation to exemplary implementations, including shadow masks, periodic masks, chirp masks, random masks, and so forth, and various other categories could be identified. As used herein, the term "random" refers to a pattern that is non-periodic over the entire length of a longitudinal sequence of filters; in contrast, a "periodic" filter assembly has at least one pattern that repeats more than once across the assembly's longitudinal length; and "chirp" patterns meet the above definition of random but can, with linearly varying time scaling, meet the above definition of periodic, in effect being a sequence of periods of linearly changing frequency or wavelength. A "shadow mask" is not a band pass filter, but rather an intensity-based filter assembly that, within a photon energy range of interest, transmits/reflects light of all energies, but with different parts of the filter transmitting/reflecting the light at different intensities, such as black and white and/or different gray scales. Any of these types of filter assemblies can be used to obtain "spatially modulated" emanating light, meaning emanating light that varies in time depending on position of an object from which it is emanating.

As used herein, the term "white", in a given implementation, refers to light with a spectrum that approximates maximum intensities across the implementation's full range of photon energies (which could be broad band, a combination of red, green, and blue, or another appropriate combination); the term "black" refers to the opposite of white, i.e. minimum available intensities across the full range, with the ideal being no light and therefore zero intensities. In emanating spectra, for example, light without maximal intensities across the full range as in white may be characterized as having a "gray level", such as one of the gray levels between white and black, or as having a "color", such as if it includes predominantly photon energies in a subrange, e.g. one of the colors in the visible range of wavelengths or in the infrared or ultraviolet ranges, or possibly a combination of such colors. Spectra that are neither black nor white are sometimes referred to herein as "non-binary spectra".

Filter arrangement 20 includes either or both of two specified combinations or configurations of filters: Filter component 30 includes filter assembly 32 in which positions 34 and 36 have different transmission functions as indicated by different cross-hatching, while filter component 40 has a combined transmission function, represented by box 42, in which two or more different non-uniform transmission functions are superimposed. As a result of the differences in transmission functions, information can be encoded in time variation of emanating light from objects such as object 10.

As used herein, the term "transmission function" refers to a function that indicates, for some appropriate position or set of positions, the relationship of output and input light of a light-transmissive and/or light-reflective component such as a filter or filter assembly. A position's transmission function could indicate, for example, ratio of output intensity to input intensity at the position across a range of photon energies, sometimes referred to herein as the transmission function's "transmission spectrum"; a band pass filter, for example, could have approximately the same transmission spectrum at substantially all of its positions. A position could have any of a variety of other kinds of transmission functions, including, for example, an "intensity ratio", indicating the ratio of the positon's output intensity to its input intensity, where the same intensity ratio applies to all photon energies across the relevant range; in the simple case in which each position of a filter has either an intensity ratio of zero or one, each position's transmission function could be one of a pair of binary values, such as black/white, ON/OFF, one/zero, or the like.

Further, a band pass filter or other filter element or assembly has a "uniform transmission function" if substantially all its positions have transmission functions that are approximately the same, and such a transmission function may be said to be "approximately uniform" for light transmitted/reflected through the filter element or assembly. Conversely, a filter element or assembly has a "non-uniform transmission function" if its transmission function is not approximately uniform; examples include periodic, random, and chirp filters as described above.

Transmission functions can, of course, be different from each other in various ways. For example, transmission functions of two positions can differ in "color", meaning that the positions have different transmission spectra; transmission functions with transmission spectra that have the same shape across a relevant range can differ in "intensity", meaning that they have different intensity ratios. Similar terminology can be applied to uniform transmission functions for filter elements, components, or assemblies. In FIG. 1, elements 34 and 36 have transmission functions that are different from each other. Also, simpler transmission functions that are superimposed to provide a combined transmission function can have different transmission functions; in FIG. 1, two of the simpler transmission functions superimposed to provide combined transmission function 42 are non-uniform and different from each other.

Different transmission functions can also be combined in a number of ways. For example, in a longitudinal sequence of filters, transmission functions are similarly combined into a sequence. In a stack or other radial sequence of filters or filter assemblies, on the other hand, transmission functions can be "superimposed", meaning that both transmission functions are applied to light passing through the component, resulting in a combined transmission function in which simpler transmission functions are superimposed. As used herein, a transmission function is "simpler" than a combined transmission function in which it is superimposed with at least one other transmission function, except in cases where the combined transmission function and all of the superimposed transmission functions have the same spectral shape or where the superimposed transmission functions have related shapes that result in uniform loss of detail when superimposed in specific phase relationships; although there are many abstract examples of superpositions that result in uniform loss of detail (e.g. two square waves of the same period and at opposite phase would have a flat line superposition) simplifying superpositions are very unlikely to occur between transmission functions with disparate shapes, such as random and periodic, random and chirped, chirped and periodic, and so forth—some detail might be lost locally in such cases, but most detail is preserved. Simpler transmission functions can be superimposed to obtain a combined transmission function in various ways other than a stack or radial sequence; for example, as described below in relation to some exemplary implementations, a single filter assembly can have a combined transmission function that is "stack-equivalent", meaning that it is approximately equivalent to a stack of filter components with simpler transmission functions. In some cases, including certain types of reflective filters, a stack-equivalent filter assembly can be equivalent to a combination of simpler filters without regard to the order in which they are superimposed, so that it is equivalent to a number of different stacks in which the simpler filters are in different orders.

As shown within combination 30, when object 10 is in segment 50 or segment 52 of its path, respective portions of emanating light are transmitted/reflected through positions 34 and 36 of filter assembly 32, as indicated respectively by arrows 54 and 56. Because of the different transmission functions, this transmitting/reflecting operation encodes information in time variation of the emanating light, represented by arrows 58. Specifically, if the emanating light from segments 50 and 52 has the same intensity or spectrum, the output light from positions 34 and 36 can affect its intensity or spectrum differently, and this difference can indicate, for example, the time at which object 10 moved between segment 50 and segment 52. In the illustrated example, segment 50 precedes segment 52 along the path of object 10, so that the portion of emanating light from segment 50 is transmitted/reflected according to the transmission function of position 34 before the portion of emanating light from segment 52 is transmitted/reflected according to the transmission function of position 36.

In some exemplary implementations below, for example, a filter assembly can have a longitudinal sequence of band pass filter elements with bands of different colors. As a result, output light from filter elements of different colors will have different intensities, depending on the spectrum of light emanating from an object, so that time variation of the output light encodes information about the emanating light's spectrum, i.e. about the type of the object. In other examples, information about speed or other displacement rate and position can be encoded by longitudinal filter sequences.

As shown within component 40, on the other hand, as object 10 passes through each of a series of segments that includes segments 60 and 62, respective portions of emanating light are transmitted/reflected with combined transmission function 42, as indicated by respective arrows 64 and 66. Because at least two of the simpler transmission functions that are superimposed in function 42 are non-uniform and different from each other, this transmitting/reflecting operation also encodes information in time variation of the emanating light, represented by arrows 68. If the emanating light from each segment in the series has the same intensity or spectrum, the output light from function 42 will be encoded in accordance with both of the simpler non-uniform transmission functions. In other words, information in accordance with both of the simpler transmission functions will be concurrently encoded in time variation of the emanating light.

In some exemplary implementations below, for example, a stack or stack-equivalent filter assembly combines a periodic or chirp transmission function that can encode information about an object's position, speed, or other displacement rate with a random transmission function that can encode information about an object's spectrum or type. Emanating light passing through the filter assembly is concurrently encoded with both types of information.

As suggested by the words "AND/OR" between combination 30 and component 40, the two are not mutually exclusive, and could be implemented together. As described below in relation to some exemplary implementations, a single filter assembly could encode information in time variation of emanating light in both of the ways illustrated for combination 30 and component 40.

The operation in box 70 photosenses the emanating light that has information encoded in its time variation, represented by arrows 58 and 68. This operation can be implemented with any suitable photosensing component, some of which are described below. In general, sensing results from photosensing take the form of analog or digital electrical signals, depending on the structure and circuitry included in the photosensing component. The operation in box 72 uses the sensing results from box 70 to obtain data indicating some or all of the encoded information, and can therefore be referred to as a "decoding" operation. The results of decoding can be used in a wide variety of ways, some of which are described below in relation to specific implementations.

Information about an object, as obtained in FIG. 1, can be used for a wide variety of purposes. In exemplary implementations described below, such information can, for example, be used to distinguish objects. In some applications, such as where the distinguished objects are registration marks in documents or other images, appropriate subsequent operations can be controlled based on the results of distinguishing objects.

Filtering arrangement 20 in FIG. 1 could be implemented in many different ways, some of which are described below. In some exemplary implementations below, for example, a filter component includes positions that have different transmission functions. In others, a filter assembly has a combined transmission function with superimposed simpler, non-uniform transmission functions. These techniques can be implemented together. As a result of these techniques, emanating light will have time variation due to different transmission functions, and the time variation of the emanating light can encode information about the object's spectral interactions such as the spectra in which it and other similar objects absorb, fluoresce, or otherwise interact with light, i.e. about the type of the object.

Figure 2:
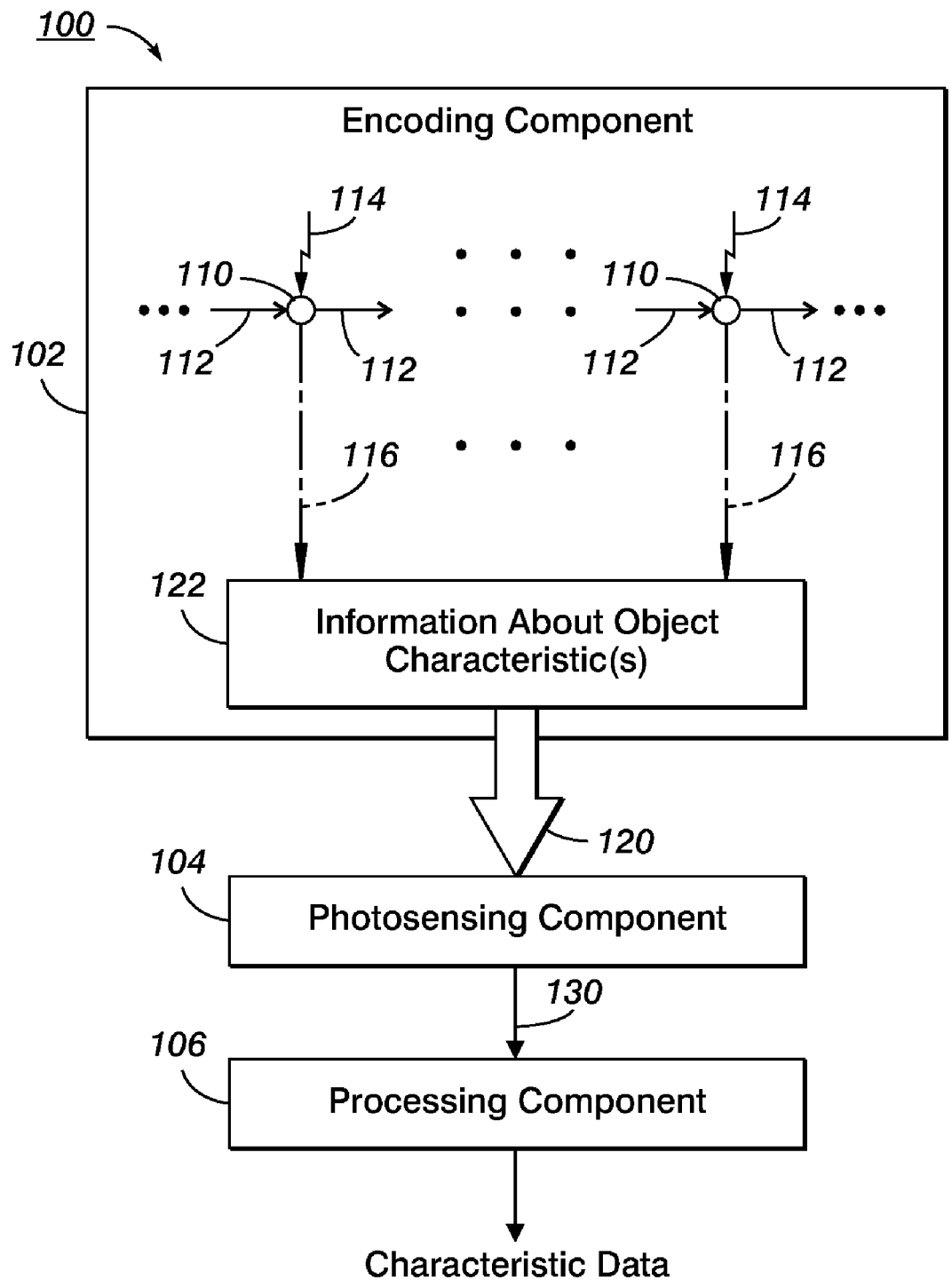
FIG. 2 is a schematic diagram showing components of a system in which light emanating from an object can include information about characteristics of the object.

FIG. 2 schematically illustrates general features of system 100, a system in which light emanating from a moving object can include information about characteristics of the object and in which features described above in relation to FIG. 1 can be implemented. As with other exemplary implementations described below, system 100 involves a combination of parts or components. Encoding component 102 illustratively provides output light that includes information about one or more object characteristics. Photosensing component 104 responds to the output light, providing sensing results such as electrical output signals with information in a form that can be communicated to processing component 106, possibly after conversion to other forms, e.g. for storage, transmission, and processing, such as optical or other electromagnetic signal forms. Processing component 106 can use the sensing results from photosensing component 104 to obtain and/or provide characteristic data indicating information about one or more object characteristics.

Object 110 illustratively travels in a direction indicated by arrows 112, passing through a succession of positions, two of which are illustrated. In some positions, object 110 can receive excitation, illustrated by arrows 114, and, in response, light as illustrated by arrows 116 can emanate, such as from fluorescence of a dye or other "tag" attached to object 110 or from native fluorescence or autofluorescence of object 110 itself, e.g. due to ultraviolet light or other excitation of intrinsic cell material or other material in object 110; except as otherwise noted, however, implementations described herein can additionally or alternatively employ chemofluorescence, biofluorescence, absorption, scattering, or other phenomena that do not require concurrent excitation. More generally, excitation could take any appropriate form and is not limited to illumination, and excitation and emanation need not be concurrent or otherwise coincident, but could have any appropriate relationship in space and time. Some examples of excitation are described below in relation to exemplary implementations.

Arrow 120 represents output light from encoding component 102. Box 122 between arrows 116 and arrow 120 illustrates that information about one or more characteristics of object 110 is included in the output light. As described below in relation to exemplary implementations, this information can be encoded in a variety of ways, including, for example, patterning excitation and/or patterning emanating light to obtain encoded output light represented by arrow 120.

Arrow 120 points to photosensing component 104, indicating that at least part of the encoded output light is illustratively sensed by component 104 to obtain sensing results. Based on the sensing results, component 104 provides electrical output signals represented by arrow 130. The electrical output signals can also include at least some of the information about object characteristics from box 120. As a result, processing component 106 can, in response to the electrical output signals, obtain and/or provide characteristic data indicating information about object characteristics.

Figure 3:
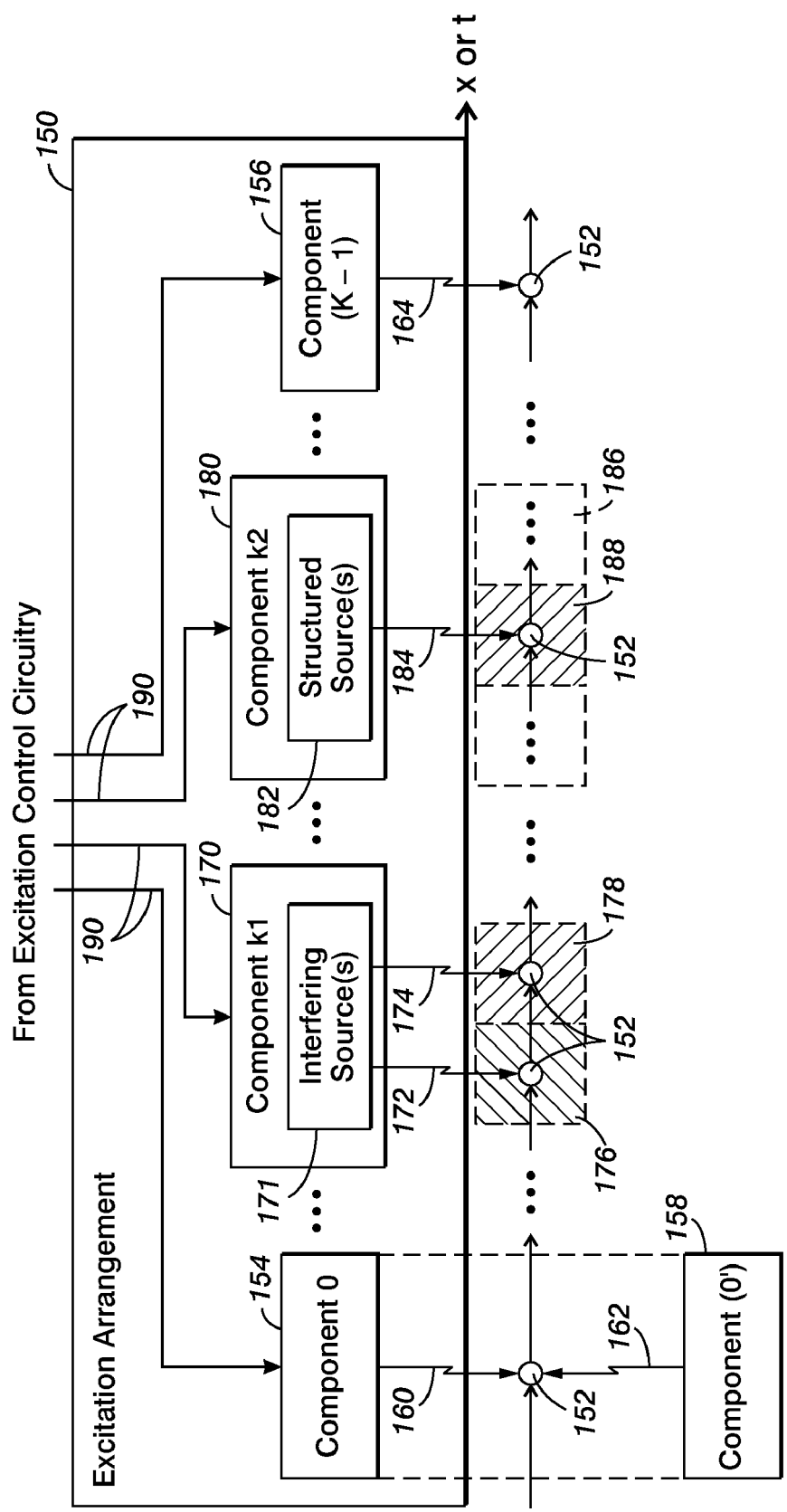
FIG. 3 is a schematic diagram of an excitation arrangement in an encoding component as in FIG. 2.
Figure 4:
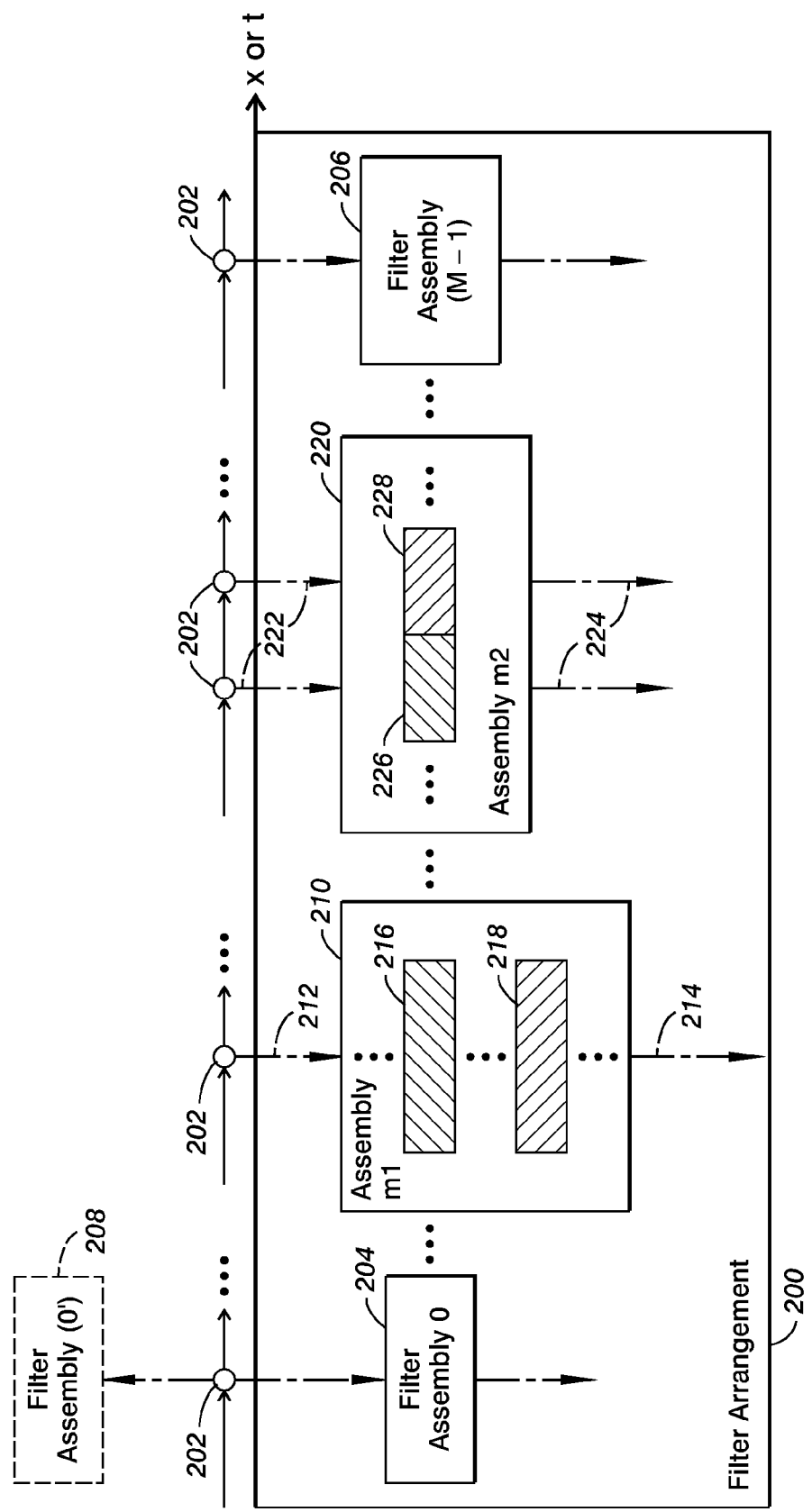
FIG. 4 is a schematic diagram of a filter arrangement in an encoding component as in FIG. 2.
Figure 5:
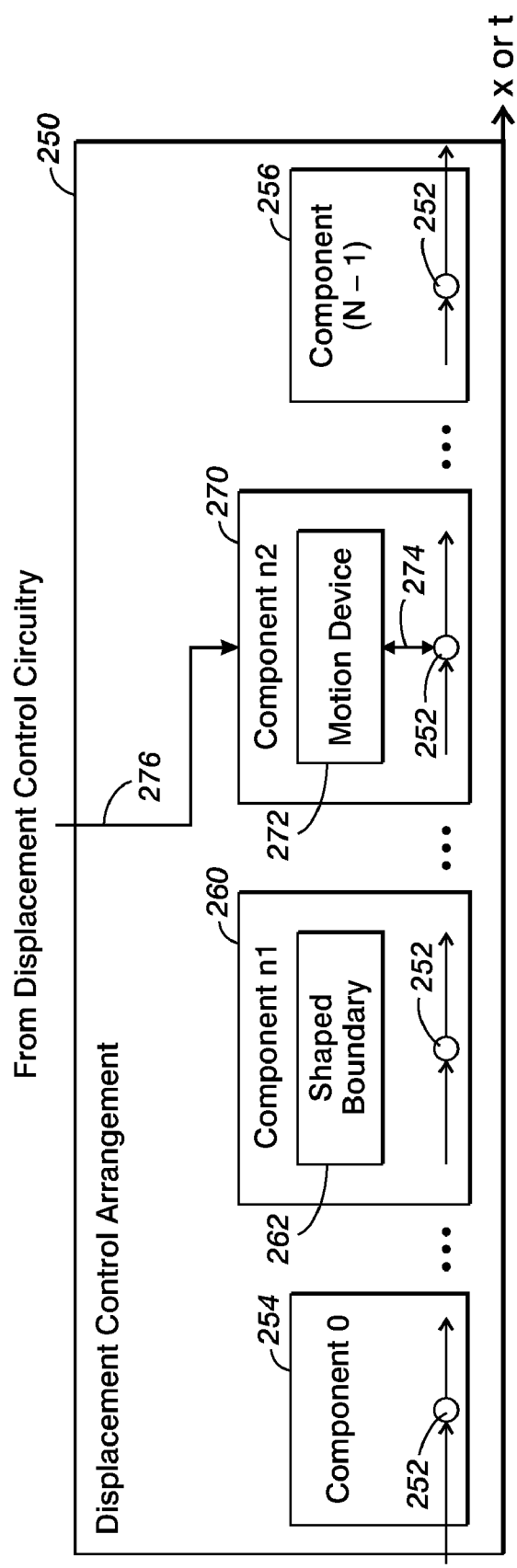
FIG. 5 is a schematic diagram of a displacement control arrangement in an encoding component as in FIG. 2.

Each of components 102, 104, and 106 in FIG. 2 could be implemented in a wide variety of different ways. FIGS. 3-5 illustrate several general features of implementations of encoding component 102, each of which involves an arrangement along a path traveled by a moving object.

In FIG. 3, excitation arrangement 150 is along a path traveled by moving object 152 as it emanates light within an encoding component such as component 102 in FIG. 2. As suggested by the one-dimensional coordinate axis labeled "x OR t", the path can be treated either as extending in space, such as along an x-direction, or as occurring over time, t; unless otherwise indicated hereafter in relation to a specific exemplary implementation, the x-direction refers to an object's path and therefore might not in some cases follow a straight line relative to the environment. Although the speed or other rate of displacement of object 152 may vary as it travels along the path, information about its speed or other rate of displacement can be sufficient to allow an approximate mapping between its x-direction positions and times t; more generally, mapping between an object's x-direction positions and times t can be based on any suitable system, such as with trigger detection techniques as described in U.S. Patent Application Publication No. 2007/0145249, entitled "Sensing Photons from Objects in Channels", incorporated herein by reference in its entirety, or from other techniques, including obtaining information such as a trigger signal from an object's encoded signal.

Although excitation components could be positioned in any appropriate way along a path, the exemplary implementations described below generally involve arrangements of one or more excitation components along the x OR t axis, and FIG. 3 shows several exemplary components within a sequence of K excitation components 154 through 156, with component 154 labeled "0" and component 156 labeled "(K−1)". Excitation components need not, however, be arranged on only one side of the path, but rather could be positioned at any suitable positions around the path, depending on how excitations from different components interact. Also, two or more excitation components could be at the same position or in overlapping position ranges along the x OR t axis, but displaced in a rotation direction; a configuration of excitation components that are sufficiently displaced in a rotation direction so that they are around the path is illustrated by component 158, representing a possible position of another excitation component labeled "(0')" in arrangement 150, on the opposite side of the path traveled by object 152 from component 154.

Arrow 160 schematically represents excitation from component 154, while arrow 162 represents excitation from component 158. Similarly, arrow 164 represents excitation from component 156. Although excitation from components 154 and 158 can be provided concurrently to object 152, as suggested by arrows 160 and 162, excitation from component 156, represented by arrow 164, is provided at a subsequent position and time of object 152.

Excitation component 170, labeled "k1", illustratively includes one or more interfering light sources 171, resulting in two or more different types of excitation, with two types represented by arrows 172 and 174. The excitation represented by arrow 172 occurs while object 152 travels along a segment of the path through region 176, while the type of excitation represented by arrow 174 occurs while object 152 travels along a subsequent segment of the path through region 178. Regions 176 and 178 therefore form a pattern in space, an example of "spatially patterned excitation" used herein to refer to excitation that occurs in a pattern in space, i.e. a "spatial pattern"; spatially patterned excitation could, for example, include multiple periods of a spatial pattern. In particular, the excitation in region 176 has a different photon energy spectrum than the excitation in region 178, so that regions 176 and 178 could be described as having "different colors" of excitation. Several specific examples in which spatially patterned excitation includes regions of different colors are described below in relation to exemplary implementations; as will be understood from some of the examples, the x-direction of a path as shown in FIG. 3 may not follow a straight line, so that regions 176 and 178 may not in fact be oriented along a straight line through components 154 through 156—in some implementations, regions 176 and 178 could each extend parallel to such a line and the path could go back and forth between regions 176 and 178.

Excitation component 180, labeled "k2", illustratively includes one or more structured light sources 182. In other words, light sources 182 are structured to provide spatially patterned excitation, represented by spatial pattern 186. In the illustrated example, arrow 184 represents excitation provided in region 188, one of a pattern of regions through which object 152 passes while receiving excitation from component 180. The complete pattern of regions is represented in FIG. 3 by pattern 186.

FIG. 3 also illustrates lines 190 through which each of components 154 through 156 can receive control signals from excitation control circuitry (not shown). For example, one or more of the components in excitation arrangement 150 could include trigger detecting circuitry (not shown) as described above, and the excitation control circuitry could, in response to the trigger detecting circuitry, provide control signals causing the component to provide excitation, either in a steady state or time-varying manner. As described below in relation to exemplary implementations, time-varying excitation can encode information in a way similar to spatially patterned excitation.

Additional description of excitation techniques is set forth in co-pending U.S. patent application Ser. No. 12/023,436, entitled "Producing Time Variation in Emanating Light", incorporated herein by reference in its entirety.

In FIG. 4, filter arrangement 200 is similarly along a path traveled by moving object 202 as it emanates light within an encoding component such as component 102 in FIG. 2. Filter arrangement 200 includes a combination of one or more filter assemblies along the path traveled by object 202.

Although filter assemblies could be positioned in any appropriate way along a path, the exemplary implementations described below generally involve arrangements of filter assemblies along the x OR t axis, and FIG. 4 shows several exemplary cross sections of filters within a sequence of M filter assemblies 204 through 206, with each cross section being taken parallel to the x OR t axis and with assembly 204 labeled "0" and assembly 206 labeled "(M−1)". Filter assemblies need not, however, be arranged on only one side of the path as shown, but rather could be positioned at any suitable positions around the path, depending on directional intensity variations of emanating light. Also, two or more filter assemblies could be at the same position or in overlapping position ranges along the x OR t axis, but displaced in a rotation direction; a configuration of filter assemblies that are sufficiently displaced in a rotation direction so that they are around the path is suggested by box dashed-line box 208 in FIG. 4, representing a possible position of another filter assembly labeled "(0')" in arrangement 200, on the opposite side of the path traveled by object 202 from filter assembly 204.

Filter assembly 210, labeled "m1", illustratively includes a radial sequence of filters through which light emanating from object 202, represented by arrow 212, can pass, with the output light from filter assembly 210 being represented by arrow 214. Filter assembly 210 could include any appropriate number of filters, with filters 216 and 218 being shown in FIG. 4.

The overall sequence of filter assemblies 204 through 206 illustrates a longitudinal sequence. Further, filter assembly 220 includes a longitudinal sequence of filters through which light emanating from object 202, represented by arrows 222, can pass, with the output light from filter assembly 220 being represented by arrows 224. Filter assembly 220 could include any appropriate number of filters in any appropriate longitudinal sequence, with adjacent filters 226 and 228 being shown in FIG. 4. Each of filters 226 and 228 could, for example, be a band pass filter, with the bands of filters 226 and 228 being sufficiently different to provide useful information about an emanation spectrum of object 202. Such a filter assembly is sometimes referred to herein as a "spatially patterned filter", because the filters it includes can be treated collectively as a single filter that has a pattern that varies as a function of position. Several examples of spatially patterned filters are described below in relation to exemplary implementations, and one or both of filters 216 and 218 in assembly 210 could also be implemented as a spatially patterned filter.

In the specific example of filter assembly 220, output light per arrows 224 can include encoded information from filters 226 and 228, and the encoded information can be recovered by photosensing the output light and performing appropriate operations on the sensing results. In general, filters 226 and 228 and other filters in filter assembly 220 can have any suitable lengths in the x OR t direction that allow recovery of the encoded information by photosensing and signal processing, including lengths smaller than the apparent extent of object 202 in the x OR t direction that may result in some loss of resolution analogous to blurriness or smearing. As described in relation to some exemplary implementations below, however, each of filters 226 and 228 can have length in the x OR t direction greater than or equal to an apparent extent of object 202 in the x OR t direction, while the lengths of filters 226 and 228 (and other filters in assembly 220) can be sufficiently small that characteristics of object 202 indicated by emanating light do not change while object 202 is traveling past assembly 220. In some specific implementations, filters 226 and 228 have parallel sides extending in a direction transverse to the path, and an assembly of such filters is sometimes referred to herein as a "striped filter" in which each stripe can be specified by filter type and its length (or width) in the lengthwise direction.

Filter arrangements similar to those shown in FIG. 4 may find application not only in fluidic implementations as described below but also in implementations in which objects in an array move relative to other components due, for example, to scanning movement. One such area of application is in image scanning, such as with scanning sheets of paper or other media that can bear images. In particular, object 202 could be a colored spot on a sheet of paper or other medium, and a filter arrangement could be used to obtain information about small differences in color of light emanating from object 202, e.g. color of reflected light in response to broadband illumination. Such information could be used to obtain position and/or color of object 202; for example, if object 202 is a registration mark with a color unique to registration marks, its color could be accurately distinguished from spots of other colors using techniques as described herein and its position could be obtained with sufficient accuracy to allow registration of the sheet, whether for image sensing or for printing or another operation on the sheet. Very high accuracy sensing of color is sometimes referred to as "hyperspectral color sensing".

In FIG. 5, displacement control arrangement 250 is similarly along a path traveled by moving object 252 as it emanates light within an encoding component such as component 102 in FIG. 2. Displacement control arrangement 250 includes a combination of one or more displacement control components, each of which is illustratively shown enclosing a respective segment of the path traveled by object 252. It would, of course, be possible to implement display control components in other ways, such as where an object travels along a path that is not enclosed within a channel or fluidic structure.

Although displacement control components could be positioned in any appropriate way along a path, the exemplary implementations described below generally involve arrangements of displacement control components along the x OR t axis, and FIG. 5 shows several exemplary components within a sequence of control components 254 through 256, with component 254 labeled "0" and component 256 labeled "(N−1)". Although each displacement control component in the sequence illustratively contains a respective segment of the path, it may be possible to implement displacement control components that affect displacement in overlapping segments of a path or that interact in other ways.

Control component 260, labeled "n1", illustratively includes shaped boundary 262, meaning that a boundary that extends partially or completely around the path, such as the boundary of a fluidic channel, has a shape that affects or controls displacement of object 252 as it travels along the path, such as by affecting its speed or other rate of displacement. Several examples of boundary shapes are described below in relation to exemplary implementations.

Control component 270, labeled "n2", illustratively includes motion device 272. Device 272 can illustratively cause lateral motion of a boundary in its segment of the path, as suggested by bidirectional arrows 274. Line 276 shows that device 272 can receive control signals from displacement control circuitry (not shown). Component 270 could also include trigger detecting circuitry (not shown), and the displacement control circuitry could respond to the trigger detecting circuitry by initiating operation of device 272, either in a steady state or time-varying manner. Examples of how device 272 could be implemented are described below in relation to specific implementations.

Figure 6:
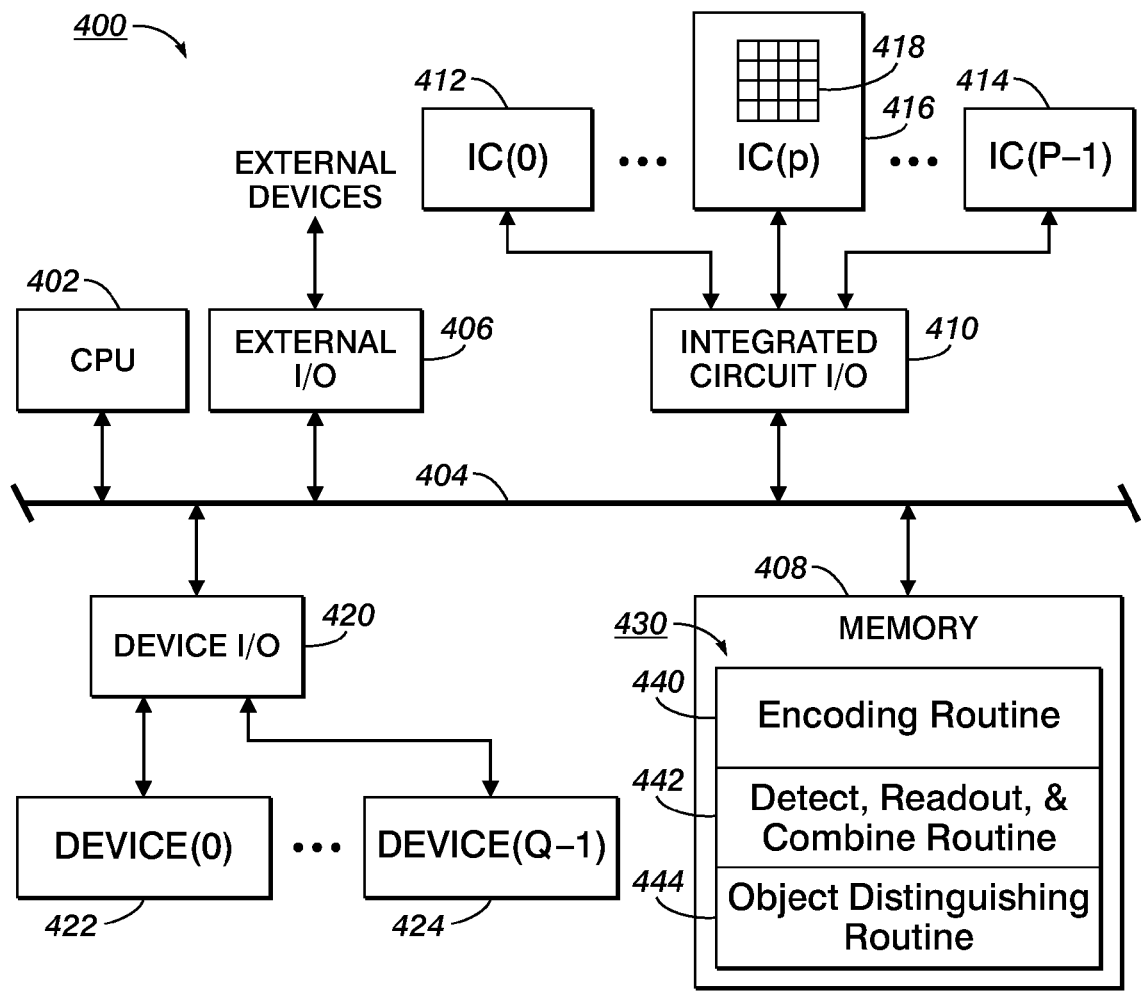
FIG. 6 is a schematic block diagram of a system in which components as in FIG. 2 can be implemented.

FIG. 6 illustrates system 400, an exemplary system that could implement components as in system 100 in FIG. 2. Although system 400 illustratively includes central processing unit (CPU) 402 connected to various components through bus 404, a wide variety of other architectures could be employed, including any appropriate combination of hardware and software, as well as specialized hardware components such as application specific integrated circuits (ASICs) for one or more of the illustrated components or in place of a software component executed by CPU 402. Furthermore, CPU 402 could be the CPU component of any suitable machine such as a laptop or desktop computer, a specialized computer for system 400, and CPU 402 and other digital components as shown could be replaced by other specialized circuitry, such as an analog signal processor; in a relatively simple application, CPU 402 could be implemented with a single digital signal processor or a CPU of a laptop or other personal computer receiving time-varying signals. On the other hand, in some applications, it may prove advantageous to implement all signal processing with analog circuitry, including operations that compare time-varying waveforms and that obtain their derivatives or other related waveforms, making it possible to replace substantially all the digital components as shown if appropriate.

System 400 also includes external input/output (I/O) component 406 and memory 408, both connected to bus 404. External I/O 406 permits CPU 402 to communicate with devices outside of system 400.

Additional components connected to bus 404 are within or connected to system 400. In the illustrated implementation of system 400, IC I/O 410 is a component that permits CPU 402 to communicate with ICs such as photosensing ICs; M ICs are illustrated in FIG. 6 by a series extending from IC(0) 412 to IC (P−1) 414. ICs 412 through 414 illustratively include IC(p) 416 with a photosensor array 418, which includes photosensing cells. Similarly, device I/O 420 is a component permitting CPU 402 to communicate with various devices in system 400, such as sensing and control devices; Q devices in system 400 are represented in FIG. 6 by device (0) 422 through device (Q−1) 424. In addition to excitation components as described above in relation to FIG. 3 and displacement control components as described above in relation to FIG. 5, devices 422 through 424 can include fluidic devices such as pumps, metering electrodes, smart gates, and other devices for gating and bifurcating, valves, flow or pressure sensors, and so forth. Such fluidic devices could be implemented in various ways; smart gates, for example, could be implemented with MEMS style microgates or by using electromagnetic forces, which are effective because most particles are charged such that an electric field can be used to direct them as desired in a channel.

Memory 408 illustratively includes program memory 430 although instructions for execution by CPU 402 could be provided in various other forms of software or hardware, on or off of CPU 402. The routines stored in program memory 430 illustratively include encoding routine 440; detect, readout, and combine routine 442; and object distinguishing routine 444. In addition, program memory 430 can also store a number of subroutines (not shown) that CPU 402 can call in executing routines 440, 442, and 444.

CPU 402 executes encoding routine 440 to encode information in light emanating from a moving object as it travels a path, i.e. information about characteristics of the object. In doing so, routine 440 can provide receive input signals from and provide output signals to devices 422 through 424. For example, to obtain appropriate motion of the object, CPU 402 can receive signals from sensors, perform computations to determine what fluidic operations are necessary, and then provide signals to activate pumps, metering electrodes, gates, and valves to produce appropriate relative movement between an object and other components of system 400 along its path. CPU 402 can also receive signals from trigger detecting devices and perform computations to determine what control signals to provide to excitation components, motion devices, or other components or devices in order to perform appropriate encoding in emanating light. Several examples of techniques that can be performed by encoding routine 400 are described below in relation to exemplary implementations.

In executing routine 442, CPU 402 can, for example, perform pre-sensing readout, obtain object information and sensing periods, perform sensing readout with sensing periods and analog adjustment, digitally adjust sensing results and store quantities for an object, and combine the quantities for an object to produce its characteristic data. Routine 442 could, for example, call a subroutine implemented as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. Such a subroutine can be implemented for single objects moving past arrays or for spaced multiple objects moving past arrays, provided spacings between objects are sufficient to avoid interference. Also, such a subroutine can follow a general strategy of performing a series of readout operations, after which information for an object is combined and its characteristic data is provided, although it would also be possible to provide the information from each readout operation immediately.

Figure 7:
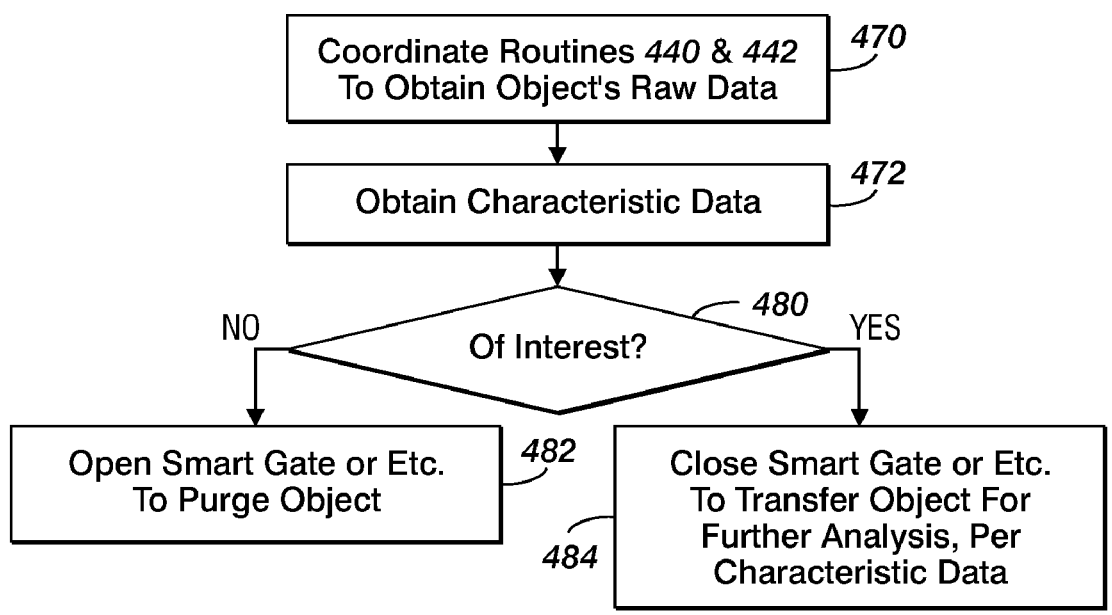
FIG. 7 is a flow chart showing general operations in an implementation of an object distinguishing routine as in FIG. 6.

FIG. 7 illustrates an example of how object distinguishing routine 444 in FIG. 6 could be implemented, using each object's raw data from routine 442 before it is used to obtain characteristic data for the object. Routine 444 can begin with the operation in box 470, which coordinates routines 440 and 442 as described above, obtaining an object's raw data, such as a data structure with photosensed quantities obtained from ICs 412 through 414.

The operation in box 472 receives the raw data from box 470, such as in the form of a handle or other item of data necessary to access a data structure. The operation in box 472 then uses the raw data to obtain the object's characteristic data, such as in one of the ways described below in relation to exemplary implementations. For example, an appropriate comparison technique could be used to obtain a comparison result indicating an object's type or other characteristic. The characteristic data from box 472 can indicate whether the object is of interest for further analysis, such as because it may be suspicious or harmful or, on the other hand, because it may be of interest for more refined analysis.

The operation in box 480 branches based on whether the object is of interest. If not, the operation in box 482 opens a smart gate or provides appropriate control signals to perform another operation to purge the object from the system. But if the object is of interest, the operation in box 484 ensures that the smart gate is closed or provides control signals for other suitable operations to transfer the object downstream so that a more refined or detailed analysis or other further analysis can be performed, possibly after concentration of the object with other similar objects by appropriate fluidic devices.

Figure 8:
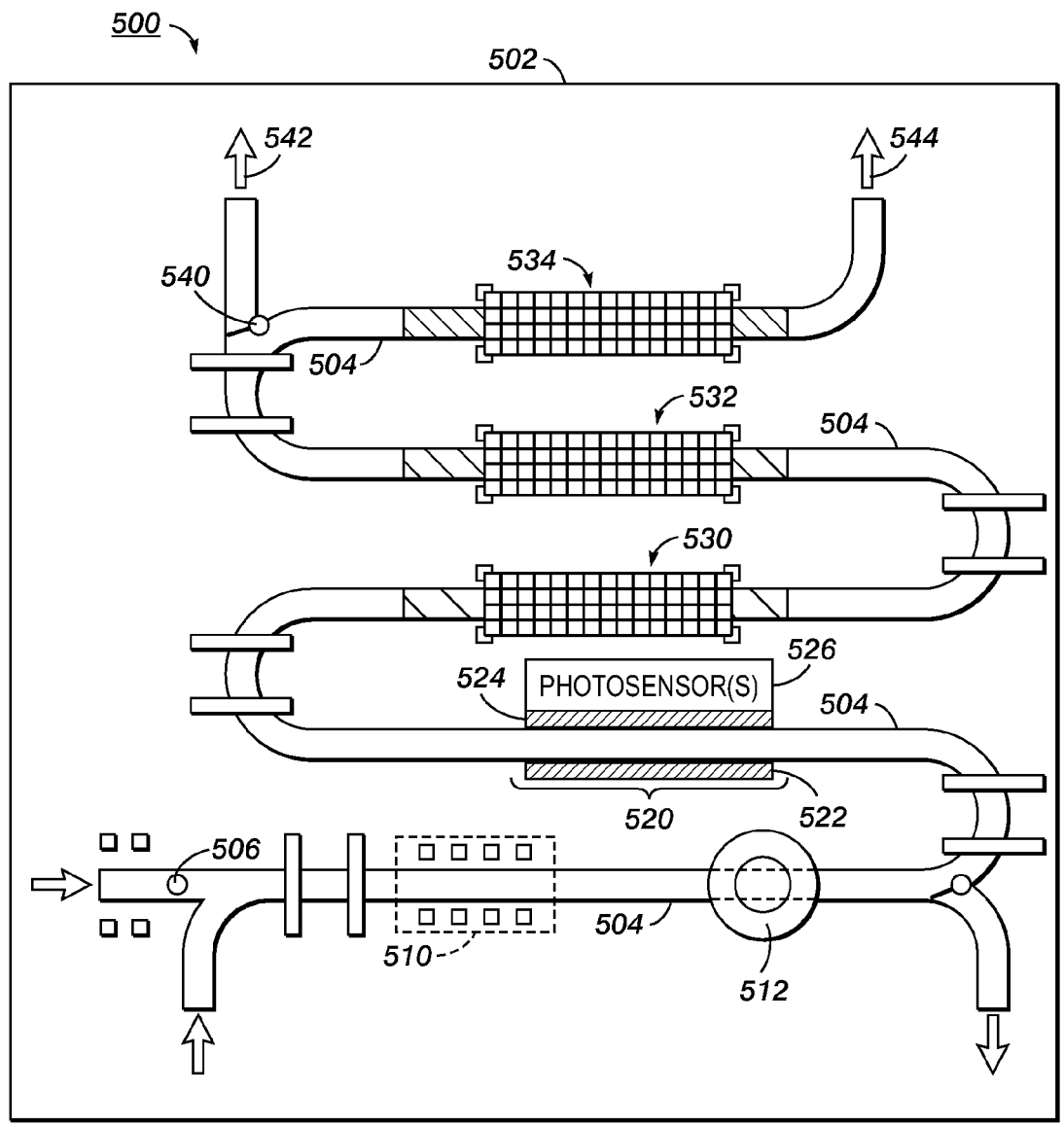
FIG. 8 is a schematic diagram of an analyzer in a fluidic structure, where the analyzer includes a system that can be implemented as in FIGS. 6 and 7.

FIG. 8 illustrates an application of a system as in FIGS. 6 and 7 in analyzer 500 on support structure 502, a fluidic structure. Defined in support structure 502 is serpentine channel 504 through which object 506 can travel, carried by fluid such as liquid, gas, or aerosol or moved in some other appropriate way. Object 506 can, for example, be a biological cell or another object of any of the types mentioned above.

The manner in which object 506 enters channel 504 and is carried by fluid can be the same as described in U.S. Patent Application Publication Nos. 2007/0145249, entitled "Sensing Photons from Objects in Channels", and 2007/0146704, entitled "Sensing Photons Energies Emanating from Channels or Moving Objects", each of which is incorporated herein by reference in its entirety. As explained there, object 506 can be carried through channel 504 by operation of propulsion components and can be purged or otherwise caused to exit, together with fluid that is carrying it, from one of several outlets, such as through toggling of valves. While in channel 504, object 506 can travel through a series of sensing components, each of which can obtain information about object 506.

The first two sensing components after object 506 enters channel 504 are illustratively Coulter counter 510, an electrically based particle size detector, and Mie scatter sensor 512, also a particle size detector. Information about size of object 506 from Coulter counter 510 and Mie scatter sensor 512 can be used in obtaining information about its other characteristics.

The next sensing component along channel 504 is emanating light encoder/photosensor 520, shown schematically in a cross-sectional view along an axis similar to the x OR t axis in FIGS. 3-5, although it would typically be implemented instead with components above and below channel 504, similarly to other sensing components described below. The schematic illustration of encoder/photosensor 520 includes excitation/displacement component 522, filter component 524, and photosensing component 526, all of which might be implemented in a variety of ways, including some of those described above and below.

After passing through encoder/photosensor 520, object 506 could be characterized without obtaining further information, or, as in the illustrated implementation, object 506 can continue through subsequent sensing components, illustratively including components 530, 532, and 534. These could, for example, include first and second fluorescence sensing components and a Raman scatter sensing component. Information obtained from any combination of the sensing components can be used to distinguish between types of objects, such as different types of biological cells, or to distinguish objects from environment or background. Based on such a distinction, valve 540 at a bifurcation junction can be toggled between two positions, with object 506 exiting as indicating by arrow 542 if valve 540 is in one position and exiting as indicated by arrow 544 if valve 540 is in another position.

The fluidic implementation in FIG. 8 is merely illustrative of a wide variety of implementations of the techniques described herein. For example, any appropriate fluidic or nonfluidic techniques could be used with a wide variety of different types of objects and various types of relative motion to gather various types of information about object characteristics.

FIG. 9 illustrates an example of article 600 with components that could be operated similarly to encoder/photosensor 520 in FIG. 8. Some features of article 600 can be understood from description in co-pending U.S. patent application Ser. No. 11/777,712, entitled "Producing Fluidic Waveguides", incorporated herein by reference in its entirety. For example, article 600 includes a "fluidic structure", used herein to refer to a structure that depends for its operation on fluid positioning or fluid flow, such as, for liquids or gases, in response to pressure or, for liquids, as a result of surface tension effects; in general, the term "fluid" is used herein to encompass all media that can flow, including liquids, gases, aerosols, and so forth. The related term "channel" refers herein to any tube or other enclosed passage within a fluidic structure through which fluid flows during operation. A channel is therefore an example of a "fluidic region", used herein to refer to a region that can contain fluid. An operation "positions" fluid in a channel if it changes the fluid's position in any way that leaves the fluid in the channel.

A channel or portion of a channel through which objects can travel along paths are treated herein as having the directional orientation described above in relation to a path. In addition, a "cross section" lies in a plane perpendicular to a direction in which a local net flow of fluid through the channel or portion can occur; a direction in which a cross section extends can be referred to as a "transverse direction" or a "lateral direction." A channel or portion with approximately uniform cross section and substantially linear longitudinal direction can be referred to as "straight", and the channels and portions described herein are generally straight unless otherwise indicated.

In order to contain fluid, a channel or other fluidic region is typically "bounded", meaning that surfaces or surface areas bound it on at least some sides. A "boundary" of a channel or portion is the surface or combination of surfaces within which fluid contained in the channel is confined. A "port" is an opening that extends through the boundary of a channel or portion such that fluid can enter or exit through the port; in general, a port is relatively small compared to the length of the channel or portion, and the boundary is treated as extending across the port as if the port did not exist.

As described below, article 600 can include two light-transmissive components, and FIG. 9 shows article 600 in a top view through one light-transmissive component. In this view, the inner region between the light-transmissive components includes two main portions, channel portion 602 that can contain fluid and non-channel portion 604 that surrounds channel portion 602; channel portion 602 is illustratively shaped like a "T", but could instead have an L-shape or any other suitable shape, including a serpentine shape as in FIG. 8. Ports 608 are openings through one of the light-transmissive components, allowing entry and exit of fluid into and out of channel portion 602.

FIG. 9 also shows filter assembly 610 in dashed outline. Filter assembly 610 is illustratively a spatially patterned filter with a longitudinal sequence of band pass filters that includes filters 612, 614, 616, 618, and 620. Filters 612, 616, and 620 are illustratively cross-hatched similarly to each other to indicate that they have the same or approximately the same band, while filters 614 and 618 are also cross-hatched similarly to each other, illustrating that they also have the same or approximately the same band, a band that is different than that of filters 612, 616, and 620. In other words, filter assembly 610 is a striped filter in which each of filters 612 through 620 can be specified by the band that it passes and its length in the x-direction in FIG. 9.

Surrounding filter assembly 610, blocking material 622 is structured and positioned to provide an aperture. Blocking material 622 can, for example, be a material with approximately zero light transmission that prevents scattering and reflection of light, also preventing light entering filter assembly 610 from nearby fluorescing objects. Blocking material 622 can be produced during the same operation that produces filters 612 through 620 and can in effect be part of filter assembly 610.

The cross section in FIG. 10 shows how light-transmissive components 630 and 632 are separated by material in non-channel portion 604. For example, components 630 and 632 can each include quartz or another suitable material such as glass or acrylic with an appropriate thickness; in a successful implementation, for example, component 630 has a thickness of approximately 0.3 mm, while component 632 has a thickness of approximately 1.0 mm or less; depending on the application, on stability of materials used, and size of objects being characterized, suitable thicknesses might range from a few millimeters down to 0.1 mm or even less. The optimum distance between them is determined primarily by the size of objects being characterized. For biological cells with typical dimensions of 10 μm, for example, the distance can be approximately 20 to 50 μm, maintained by material in non-channel portion 604, which could, for example, be a suitable photoresist material such as SU-8 or another polymer material. Alternatively, a wall (not shown) could be formed around channel portion 602, and non-channel portion 604 could then be filled with epoxy material that seals a lateral boundary around channel portion 602. Various other techniques could be used to produce a similar fluidic structure, including hot embossing, nano-imprinting, or injection molding, and channel portion 602 can have appropriate dimensions, such as for waveguiding as described in co-pending U.S. patent application Ser. No. 11/777,712, entitled "Producing Fluidic Waveguides", incorporated herein by reference in its entirety.

FIG. 10 also shows object 640 from which light is illustratively emanating upward, as illustrated by an emission cone. Although the emission cone is illustratively shown as a single cone, the actual emission cone would depend on angles of total internal reflection at surfaces through which emanating light is transmitted in article 600. FIG. 10 illustrates three alternative filter assembly positions, with filter assembly 642 facing channel portion 602, on the lower surface of component 630; with filter assembly 644 being outside of channel 602 on the upper surface of component 630; and with filter assembly 646 being spaced apart from the upper surface of component 630, adjacent photosensor 648, which could, as in other implementations, be a single, large area photosensor (such as a photo-diode, an avalanche photo-diode (APD), or a photo-multiplier tube (PMT)), or an appropriate array of photosensing cells whose sensed quantities can be combined to obtain a single photosensed quantity, such as an intensity value for a sensing period. As suggested in FIG. 10, the emission cone from object 640 is imaged onto image plane 650 extending through filter assembly 646 by optical component 652, illustratively shown as a single lens, but which could be any suitable lens, lens system, or other optical component, some examples of which are described in co-pending U.S. patent application Ser. No. 11/698,409, entitled "Method and System Implementing Spatially Modulated Excitation or Emission for Particle Characterization with Enhanced Sensitivity", incorporated herein by reference in its entirety.

The emission cone for filter assembly 642 includes the range of angles of incident light that are not totally reflected by the surface of assembly 64. Similarly, the emission cone of filter assembly 644 is determined by the range of angles within which emanating light is not subject to total internal reflection at the surface between component 630 and assembly 644. The emission cone for filter assembly 646 is similar to that for filter assembly 644, but can occupy a smaller area on filter assembly 646 due to the effect of optical element 652.

In one illustrative example, channel portion 602 contains water with an index of refraction n=1.33, and object 640 has a diameter d=7 μm, which would be typical for certain biological cells, e.g. T-lymphocytes. Channel portion 602 has a height between components 630 and 632 of 30 μm and its distance from the lower surface of filter assembly 642 is approximately h=15 μm. Component 630 is acrylic with an index of refraction n=1.48, surrounded by air with an index of refraction n=1. If filter assembly 642 were absent, the escape angle from channel portion 602 to component 630 would be α(escape)=48.75°, which would determine the size of the emission cone in which light from object 640 can leave channel portion 602. The angle of total internal reflection at the upper surface of component 630, on the other hand, can be obtained as α(TIR)=42.51°, which determines the size of the emission cone for light that leaves component 630. The diameter of a disk illuminated by object 640 at the water-acrylic interface can be obtained from D=d+2*h*tan(α(escape))= (7+(2*17.1))μm=41.2 μm, where 17.1 μm is the radius of the maximum emission cone that can pass through component 630 without total internal reflection. The "minimum feature size" ("MFS") for a pattern suitable to detect object 640 at the water-acrylic interface would be equal to D or approximately 40 μm; in general, MFS can be defined for a mask along the path of an emanating particle as the extent in the path's longitudinal direction of the mask's smallest uniform feature (i.e. the smallest transmitting filter element or the smallest blocking filter element, whichever is smaller).

Where photosensor 648 is implemented with a numerical aperture that makes the emission cone smaller, filter assembly 642 can accordingly have a slightly smaller MFS than calculated as above; similarly, in some acrylic implementations of component 630, some light typically leaves component 630 at an angle slightly higher than α(TIR), which could also allow a slightly smaller MFS. In general, however, the MFS of filter assembly 642, if too small, results in passage of light from an object's emission cone around both sides of a feature in assembly 642, so that the time-varying signal of a photosensor, while containing some information, may not accurately indicate information about displacement of the object as it travels along a path past filter assembly 642. Similar considerations apply to filter assemblies 644 and 646, with the MFS of filter assembly 644 necessarily being significantly larger than that of filter assembly 642, but with the MFS of filter assembly 646 possibly being intermediate between those of assemblies 642 and 644, depending on the precision of optical component 652. In implementations without optical components, photosensor 648 could be slightly larger due to spreading of emanating light. For a biological cell on the order of 10 μm, a typical MFS would be in the range of 10-20 μm. The channel width might be an order of magnitude larger, while the channel length might be two orders of magnitude larger, and the width of the filter assembly would depend on the channel width. For example, assembly 642 might be 100 μm wide and approximately 1.0 mm long. At the time of manufacture, a calibration operation could be performed using objects that are, for example, tiny beads with known fluorescence spectra; light emanating from such beads could be measured and used to obtain calibration values necessary to adjust measured values to obtain known intensities for such objects.

Figure 11:
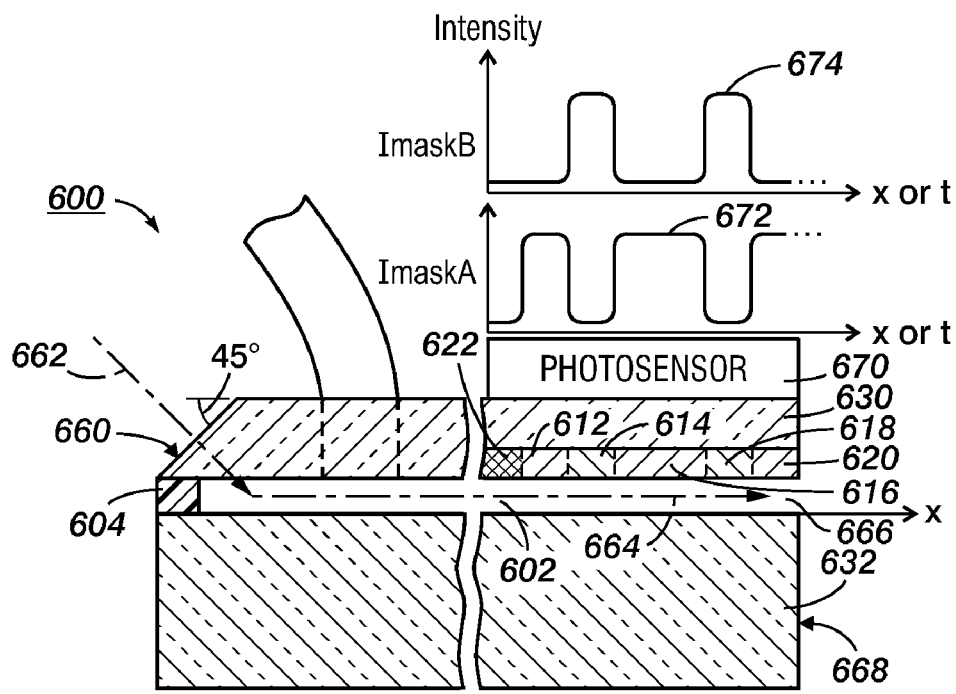
FIG. 11 is a cross-sectional view of another implementation of an article similar to that in FIG. 9, taken along the line 11-11, together with graphs of sensed intensities.

The cross section in FIG. 11 further illustrates how component 630 has oblique surface 660, a light interface surface that is illustratively at an angle of approximately 45° to the inward-facing surfaces of components 630 and 632. As a result, incident excitation light at a direction approximately perpendicular to surface 660, as illustrated by arrow 662, can cause and couple with light propagating through channel portion 602, as illustrated by arrow 664, as described, for example, in co-pending U.S. application Ser. No. 11/777,712, entitled "Producing Fluidic Waveguides", incorporated herein by reference in its entirety. Excitation light could have any appropriate wavelength, such as 266 nm, for example. The distance from surface 660 to obtain appropriate homogeneity can be determined, as described, for example, in U.S. Patent Application Publication No. 2008/0013877, incorporated herein by reference; the distance can also be sufficient to allow integration of blocking material 622.

In the illustrated implementation, the end of channel portion 602 at right in FIG. 11 is open, providing an additional port 666 through which fluid can enter into or exit out of channel portion 602. Alternatively, article 600, instead of ending at transverse end-surface 668, could extend to another area with ports similar to ports 608, such as with a part symmetrical about the position of surface 668; in this case, fluid could flow through channel portion 602 between ports 608 and similar ports at the opposite end of channel portion 602.

In the implementation in FIG. 11, the filters within filter assembly 610 are shown in cross section, and, in this implementation, the filters do not overlap, but rather are adjacent to each other. They could, for example, be integrated into a recess in the lower surface of component 630 such that they are even with the surrounding surface of component 630 or they could be surrounded on all sides by a layer of shadow (light blocking) or transparent material of the same thickness; in either of these approaches, the filters could be implemented so that there is no step at the edges of assembly 610. The size of the gap, if any, between adjacent filters depends, for example, on the resolution of the technique used to produce the filters. If the filters are produced by printing two different light-absorbing materials that have different absorption spectra (in which case a surrounding layer of shadow or transparent material could also be printed around them), the registration and gaps between filters depend on the resolution of the printing technique used; examples of such techniques are described in U.S. Patent Application Publication No. 2007/0172969, entitled "Additive Printed Mask Process and Structures Produced Thereby", and in co-pending U.S. patent application Ser. No. 11/755,717, entitled "Surface Energy Control Methods for Color Filter Printing", each of which is incorporated herein by reference in its entirety. In general, however, the techniques described herein do not require highly precise positioning of filters—a small gap between filters should not significantly affect time-varying signals that result from an object traveling past such filters while it emanates light.

The upper part of FIG. 11 includes two graphs illustrating intensities detected by photosensor 670 in response to two types of objects, one emanating light of color "A", the other emanating light of color "B". Filters 612, 616, and 620 have bands that allow light of color "A" to pass, while filters 614 and 618 have bands that allow light of color "B" to pass.

Curve 672 illustrates intensities indicated by sensing results from photosensor 670 if object 640 emanates light of color "A" as it travels along the path through channel portion 602. In other words, the emanating light's photon energy distribution matches the band for filters 612, 616, and 620 so that curve 672 is high along those filters but low along filters 614 and 618; its high value is indicated on the vertical axis as "ImaskA".

Curve 674, on the other hand, illustrates intensity indicated by sensing results from photosensor 670 when object 640 emanates light of color "B" as it travels along the path. In this case, the emanating light has a photon energy distribution that matches the band for filters 614 and 618 but not for filters 612, 616, and 620, so that curve 674 is at a high intensity along filters 614 and 618, "ImaskB", and at a low intensity elsewhere.

Curves 672 and 674 illustrate an example in which two different types of objects provide signals that are approximately complementary, except at the far left along blocking material 622 where both curves are at approximately zero intensity. In a simple implementation, for example, filters 612, 616, and 620 could be red band pass filters, filters 614 and 618 could be green band pass filters, each object could either be a red fluorescing particle or tag, i.e., emanating light of color "A", or a green fluorescing particle or tag, i.e., emanating light of color "B". As suggested, curves 672 and 674 could be plotted based on the x-direction position of object 640 or based on the t-position within the time varying output signal from photosensor 670, which could be provided continuously or by any suitable form of sampling, such as by periodic readout at an appropriate frequency. The high intensities of curves 672 and 674 would be reduced to the extent that blocking material 622 prevents light from reaching photosensor 670.

As a result, output signals from photosensor 670 can be used to distinguish types of objects, in this case to distinguish objects that emanate light of color "A" from objects that emanate light of color "B", and examples of techniques that distinguish types of objects in various ways are mentioned below in relation to exemplary implementations. In some examples, emanating light encoded by a filter assembly with stripes of random lengths can be analyzed by comparing a resulting time-varying signal with one or more templates or other signals to determine an object's type, displacement, and position to a high level of precision.

Figure 12:
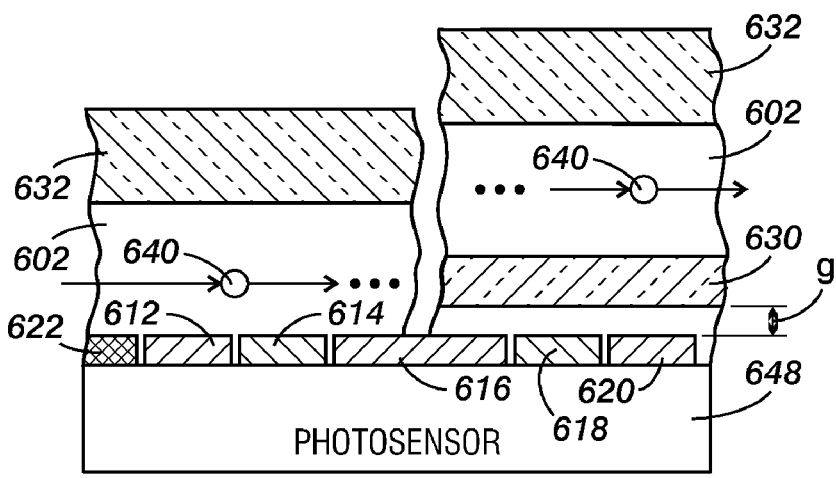
FIG. 12 is a partially schematic cross-sectional view showing two ways in which a filter arrangement on a photosensitive surface can be configured in an encoding component as in FIG. 2.

FIG. 12 illustrates two alternative implementations similar to those in FIGS. 9-10, and with the same reference numerals, but with filter assembly 610 on a photosensitive surface of photosensor 648. These implementations could be implemented by printing or otherwise depositing and patterning filters 612, 614, 616, 618, and 620 and blocking material 622, such as in the manner described above, or by producing a longitudinal sequence of band pass filters in any other appropriate way, with some possible techniques being described below in relation to other exemplary implementations. In the implementation at left, photosensor 648 also operates as one side of channel portion 602, replacing light-transmissive component 630 along at least a portion of the channel. In other words, filter assembly 610 is positioned similarly to filter assembly 642 in FIG. 10, allowing a very small MFS. In the implementation at right in FIG. 12, photosensor 648 is outside of channel portion 602 separated from the outer surface of component 630 by a small gap of height g as shown. In this implementation, filter assembly 610 is positioned similarly to filter assembly 644 in FIG. 10, but not directly on the outer surface of component 630, so that a larger MFS is necessary. The gap between component 630 and photosensor 648 can be maintained by spacers or other appropriate support components, and can be sufficiently large that photosensor 648 does not interfere with anti-resonant waveguiding within channel portion 602, which can be implemented, for example, in the ways described in co-pending U.S. patent application Ser. No. 11/316,660, entitled "Providing Light to Channels or Portions", incorporated herein by reference in its entirety.

Absorption filters as described above in relation to FIGS. 9-12 can be implemented in a multitude of ways. For example, rather than only two types of band pass filters that have bands for respective colors, three or more types of filters with three or more respective colors could be used. Similarly, a filter assembly can include band pass filters and other types of absorption filters as would be found in a shadow mask. Furthermore, with printed filters as described above or with other filters produced with layers of material, overlapping band pass filters could be produced, providing additional information. In addition, absorption filters could be combined with reflection filters, as described below in relation to some exemplary implementations.

Figure 13:
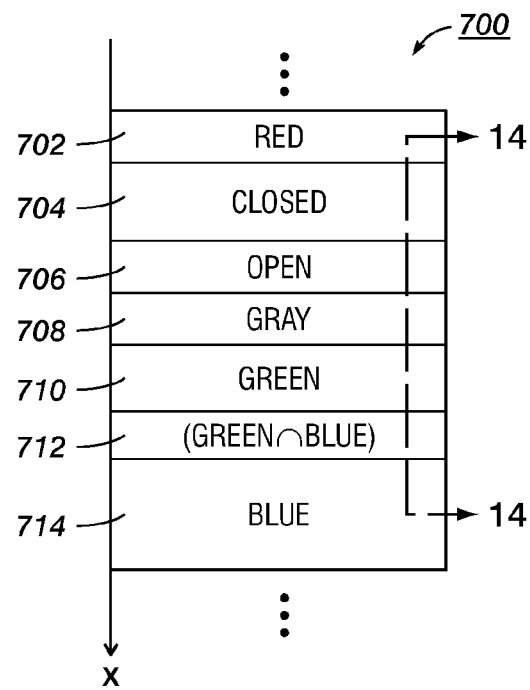
FIG. 13 is a schematic top view of another filter arrangement that can be included in an encoding component as in FIG. 2.

Filter assembly 700 in FIG. 13 illustrates some of these variations. In the illustrated assembly, each stripe is labeled with a description of its filter criterion. Stripe 702 is a red band pass filter; stripe 704 is a closed filter, meaning that it allows no transmission; stripe 706 is an open filter, meaning that it allows full transmission; stripe 708 is a gray filter, meaning that it passes all photon energies across a range of interest, but at an intensity in between an open filter and a closed filter; stripe 710 is a green band pass filter; stripe 712 is a combined band pass filter that passes only the intersection of blue and green; and stripe 714 is a blue band pass filter. In addition, as can be seen, the widths of the stripes are random rather than periodic.

Figure 14:
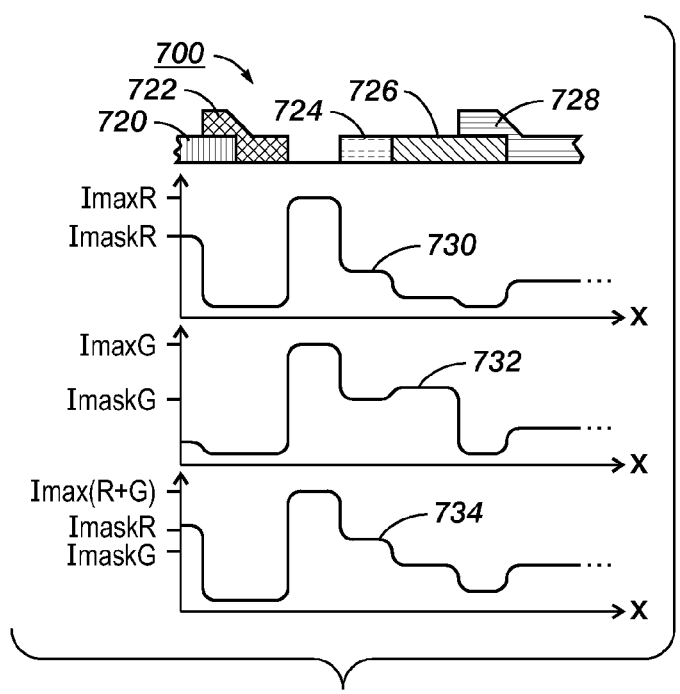
FIG. 14 is a cross-sectional view of an implementation of a filter arrangement similar to that in FIG. 14, taken along the line 14-14, together with graphs of transmitted intensities.

The cross section in FIG. 14 illustrates one way of implementing filter assembly 700 in FIG. 13, illustratively using patterned layers of light absorbing material to produce different types of filters. The implementation in FIG. 14 could, for example, be implemented by printing or otherwise depositing and patterning layers of material as described above.

In the cross section at the top of FIG. 14, filter assembly 700 includes red layer part 720, black layer part 722 overlapping layer part 720, gray layer part 724, green layer part 726, and blue layer part 728 overlapping layer part 726. Where overlaps occur, the result is the intersection of two absorption filters: the intersection of layer parts 720 and 722 is a closed filter, while the intersection of layer parts 726 and 728 is a filter with a band that is the intersection of the bands of the green and blue filters.

The three graphs below the cross section show expected intensity signals similar to those in the graphs in FIG. 11. Curve 730 would be for a red fluorescing particle or tag; curve 732 would be for a green fluorescing particle or tag; and curve 734 would be for an example where object 640 is tagged both with a red and a green fluorescing particle so that curve 734 is a scaled sum of curves 730 and 732. More generally, the technique of FIGS. 13 and 14 would make it possible to distinguish not only red, green, and blue particles and tags, but also objects tagged with combinations such as red and green, green and blue, red and blue, and red and green and blue. Each combination results in a distinguishable time varying signal that can be analyzed to obtain information about the color or colors that are emanating.

Although the intensity signals described above in relation to FIGS. 11 and 14 could be obtained from sensing results of a single, large area photosensor, it would also be possible to use an IC with an array of photosensing cells or an array of discrete photosensors, in either case appropriately positioned along a path traveled by objects past one or more filter assemblies. If an array is used, and each element of the array is covered with a different filter assembly, it may be possible to distinguish many different types of particles concurrently. The number of particles to be distinguished can be much larger than the number of elements in the array, since each measurable distinguishing feature can provide one axis in a principal component analysis, and multiple particles can be distinguished along each such axis. Additional techniques that can be used to track and distinguish objects are described in co-pending U.S. patent application Ser. No. 11/702,328, entitled "Distinguishing Objects", incorporated herein by reference in its entirety. Objects can be distinguished, for example, from their environment or background or from objects of other types; an operation "distinguishes" objects if the operation locates, selects, sorts, counts, or otherwise identifies an object or controls or directs an object according to type or separates objects or otherwise treats objects differently in some way.

Band pass filters of other types can also be used to implement filter assemblies as described in some of the exemplary implementations herein. For example, interference based filters can have different bands similar to the bands described above in relation to FIGS. 9-14.

Figure 15:
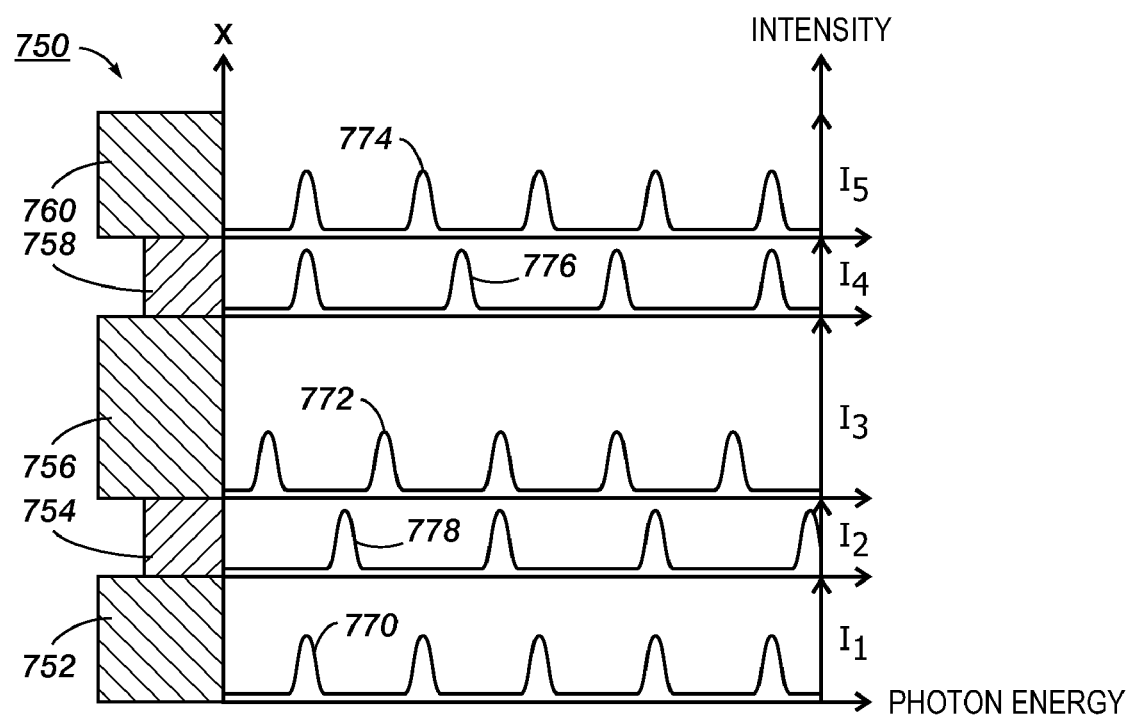
FIG. 15 is a cross-sectional view of another implementation of a filter arrangement that can be included in an encoding component as in FIG. 2, together with graphs showing spectra of transmitted intensities.

Filter assembly 750 in FIG. 15 illustrates an implementation in which a thin layer of transparent material creates Fabry-Perot oscillations, and can be structured to obtain high thickness-dependent index contrast. Assembly 750 includes filters 752, 754, 756, 758, and 760, each of which has substantially constant thickness, but with the thicknesses of filters 752, 756, and 760 being approximately equal to each other while the thicknesses of filters 754 and 758 are approximately equal to each other but smaller. Assembly 750 could be produced, for example, by etching a deposited layer of transparent material or by imprinting a non-solid layer of such material before it solidifies.

To the right of the cross section of assembly 750 is a graph showing an intensity-energy function of its transmitted light. In other words, curves 770, 772, and 774 are approximately the same because filters 752, 756, and 760 have approximately the same thickness. On the other hand, curves 774 and 776 are also similar to each other but different than the others, because the thicknesses of filters 754 and 758 are the same as each other but different than the others. As a result, an object traveling along a path past assembly 750 results in a time-varying signal with changing intensity-energy function. The total transmission at each position will relate to the overlap of the cavity's transmission lines and the particle spectrum. The other part of the emanating light would be reflected from assembly 750, and could also be detected to obtain confirming information. For example, assembly 750 could be on one cover slide of a channel, and two photosensors (not shown) could be positioned, one on the side of assembly 750 away from the channel and the other on the opposite side of the channel to obtain sensing results for the reflected emanating light.

Figure 16:
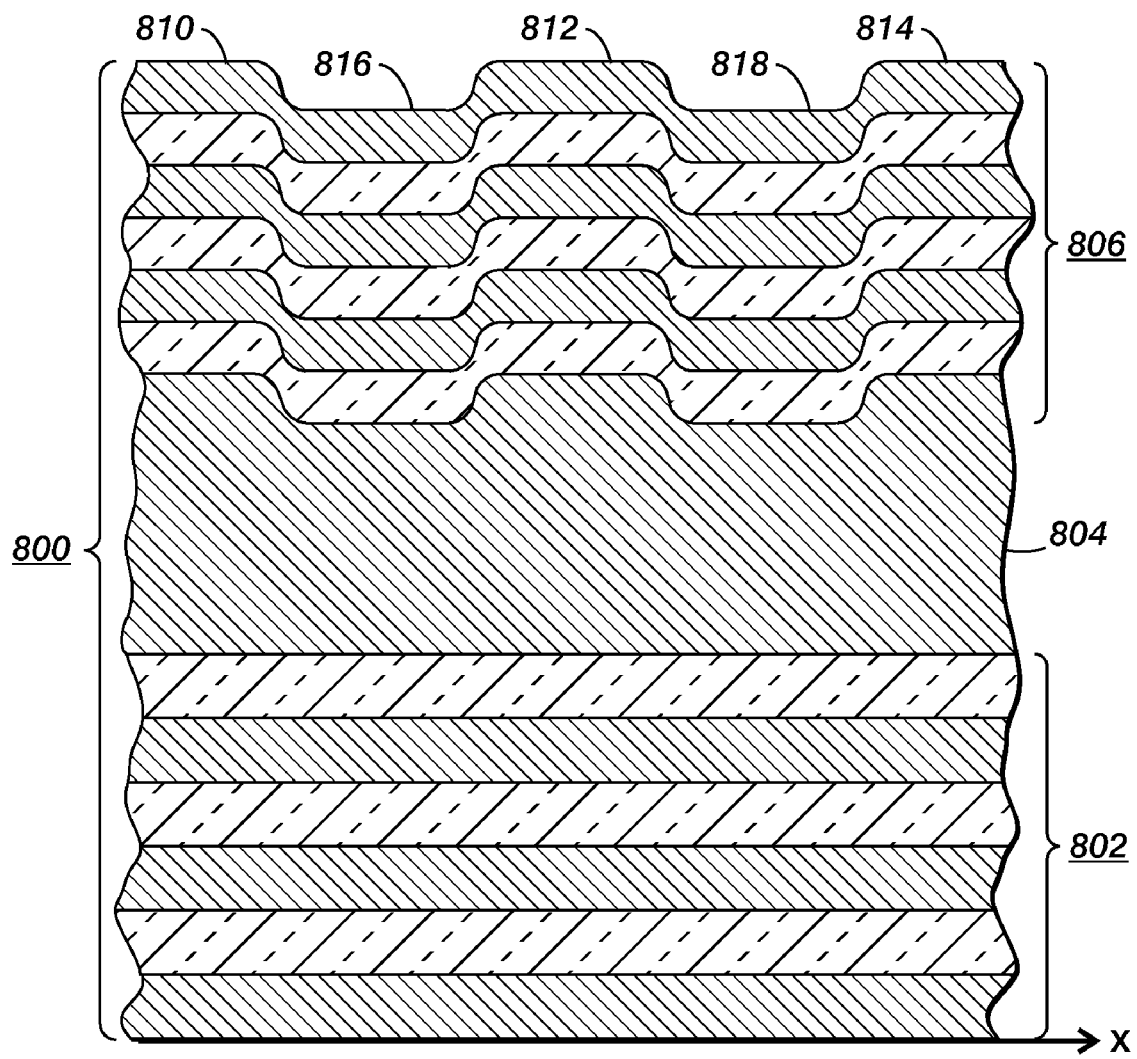
FIG. 16 is a cross-sectional view of yet another implementation of a filter assembly that can be included in an encoding component as in FIG. 2.
Figure 17:
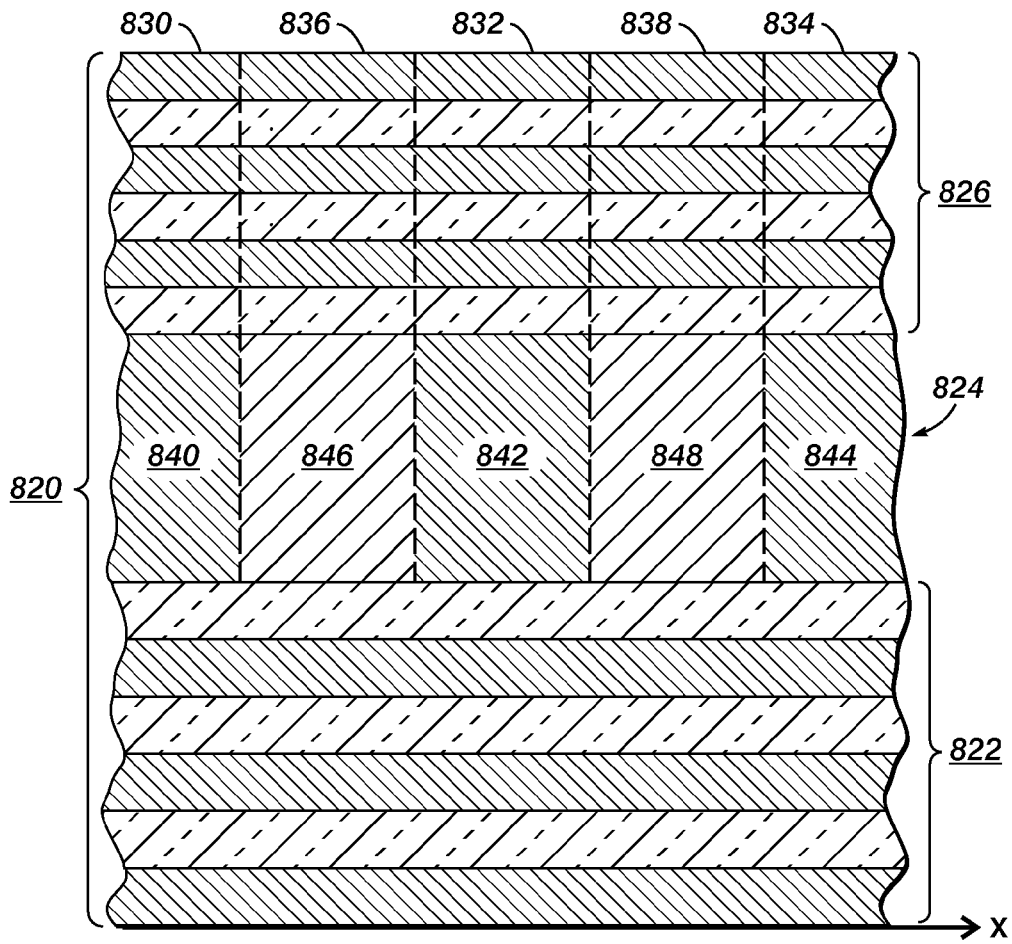
FIG. 17 is a cross-sectional view of yet another implementation of a filter assembly that can be included in an encoding component as in FIG. 2.

FIGS. 16 and 17 illustrate two ways in which Fabry-Perot interference-based filters could be structured to obtain band pass filters more nearly similar to those of FIGS. 9-12. In each implementation, optical thickness of the filter's cavity varies in the x-direction, but the variation in optical thickness is produced in two different ways. The general strategy in FIGS. 16 and 17 is to provide regions that operate as band pass Fabry-Perot filters, with different sets of filters having transmission peaks at different photon energies. For example, one set of filters could have a transmission peak at approximately 822 nm, while another could have a transmission peak at approximately 833 nm, and the two sets could have a periodic pattern as shown or any other appropriate pattern.

Filter assembly 800 in FIG. 16 includes homogeneous bottom distributed Bragg mirror (DBR) 802, cavity 804, and upper DBR 806. Such a filter assembly could be produced by using techniques described in U.S. Pat. No. 7,315,667, entitled "Propagating Light to be Sensed", incorporated herein by reference in its entirety. As can be see in FIG. 16, however, the optical thickness of cavity 804 has been modified by changing between two thicknesses, one larger and one smaller, so that assembly 800 effectively includes two sets of filters: reference numerals 810, 812, and 814 indicate three filters with the larger thickness while regions 816 and 818 are filters with the smaller thickness, therefore transmitting a shorter wavelength than the filters in regions 810, 812, and 814. The variations in thickness of cavity 804 can be produced, for example, by etching the layer in which cavity 804 is formed after it is deposited and before the series of layers in DBR 806 are deposited. Alternatively, a half-tone mask could be used during growth of cavity 804.

Filter assembly 820 in FIG. 17 similarly includes lower DBR 822, cavity 824, and upper DBR 826, each of which illustratively has approximately uniform thickness, but with cavity 824 having optical thickness that varies in the x-direction. As a result, regions 830, 832, and 834 transmit a different photon energy than regions 836 and 838. More specifically, the refractive index of cavity regions 840, 842, and 844 is different than the refractive index of regions 846 and 848. Differences in refractive index could be produced in a wide variety of ways. Implantation or ion diffusion (as in ion exchange) could be performed as is done in fabricating waveguides for integrated optics; another approach would be implantation-induced intermixing of multiple quantum well (MQW) structures as in laser diode fabrication; further, ultraviolet light-induced changes in refractive index could be used as with germanium-doped glass used in fabricating fiber Bragg gratings (FBG) in glass fibers; in principle, any technique that can modify refractive index by implantation, heat, light, or other operation could be used.

Figure 18:
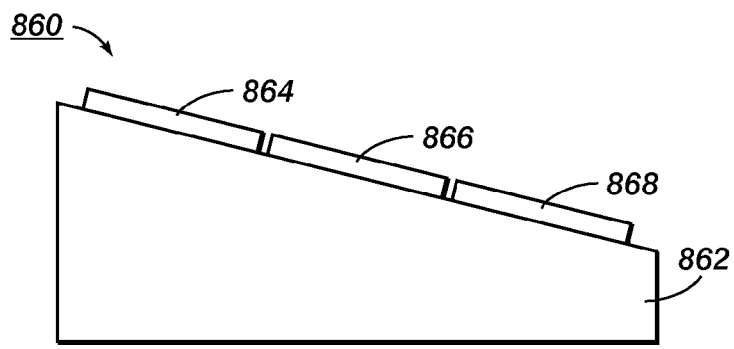
FIG. 18 is a cross-sectional view of yet another implementation of a filter assembly that can be included in an encoding component as in FIG. 2, such as with features as in any of FIGS. 15-17.

FIG. 18 illustrates an additional technique that could be used together with the technique of FIG. 15 and possibly the techniques of FIGS. 16 and 17. Filter component 860 includes a wedge-shaped layer of transparent material as in FIG. 15 or Fabry-Perot filter as in FIGS. 16 and 17, but with filter assemblies 864, 866, and 868 formed at its upper surface such as by techniques described in relation to FIG. 15, 16, or 17. In other words, in addition to having filters of the types described above, there is also a continuously varying thickness across component 860 so that, in addition to the time-varying effects of each filter assembly, additional spectral information is contained in the encoded emanating light, and can be obtained by appropriate processing. With techniques such as this, it may be possible to measure the entire spectrum with a loss of not more than 50% (assuming full modulation) of the light, which would be advantageous in comparison with conventional linear variable filter approaches.

In implementations as in FIGS. 9-12, laminar flow can be used to provide substantially uniform object speed past a filter arrangement. In contrast, FIGS. 19-21 illustrate examples in which laminar flow can produce non-uniform displacement or can be modified in other ways.

Figure 19:
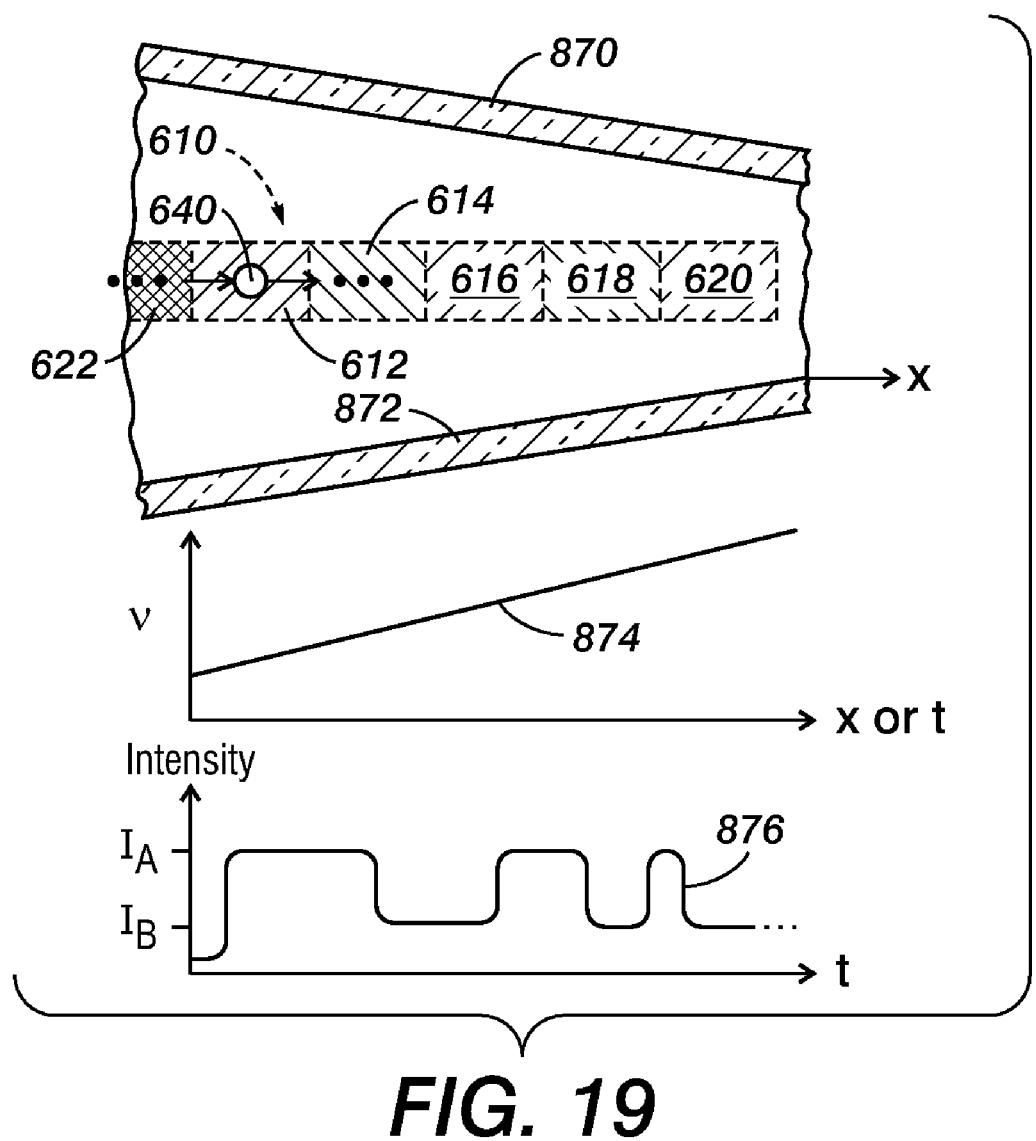
FIG. 19 is another partially schematic cross-sectional view showing a displacement control arrangement that includes shaped boundaries, together with graphs showing velocity of an object and also showing intensity of emanating light as a function of time.

FIG. 19, taken along a line similar to line 19-19 in FIG. 12, shows wall-like parts 870 and 872 with linearly decreasing distance between them. As a result, as object 640 passes along two-color filter assembly 610 (with filter elements 612, 614, 616, 618, and 620 illustratively periodic rather than random as in FIG. 12), its velocity increases linearly as indicated by curve 874, either as a function of position or of time. Therefore, rather than a periodic time-varying signal, the resulting time-varying signal is chirped, meaning that the periods decrease linearly due to change in velocity of object 640 due to change in the flow speed of fluid in the channel resulting from the changing channel dimensions. Curve 876 illustrates the resulting chirped signal, which has intensity I(A) during regions 612, 616, and 620, and intensity I(B) during regions 614 and 618. As can be seen, the duration of the signal during each successive region is shorter than the preceding region, resulting in the chirped pattern. For the sake of illustration, the linear decrease in transition time is exaggerated in curve 876 in comparison to the narrowing of the channel.

The technique in FIG. 19 is only one of a variety of ways of producing a chirped time-varying signal, and various other techniques could be used. For example, more complex flow speed distributions could be obtained by modifying the channel walls in other ways or by providing devices that change the flow speed or flow pattern within the channel, any of which would produce more complex time-varying signals from different objects.

Figure 20:
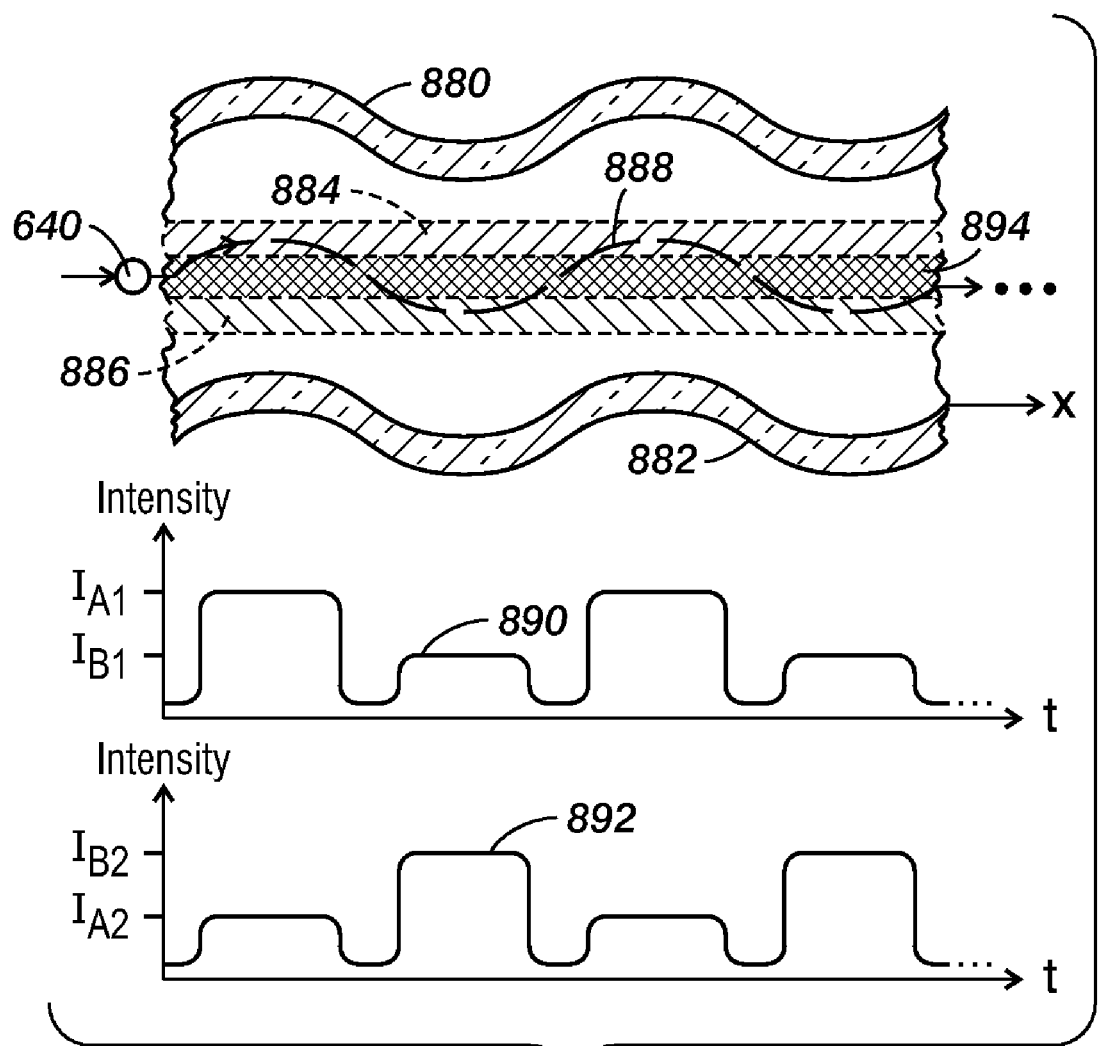
FIG. 20 is a cross-sectional view of another displacement control arrangement that can be included in an encoding component as in FIG. 2, together with graphs showing intensity of emanating light for exemplary types of objects.
Figure 21:
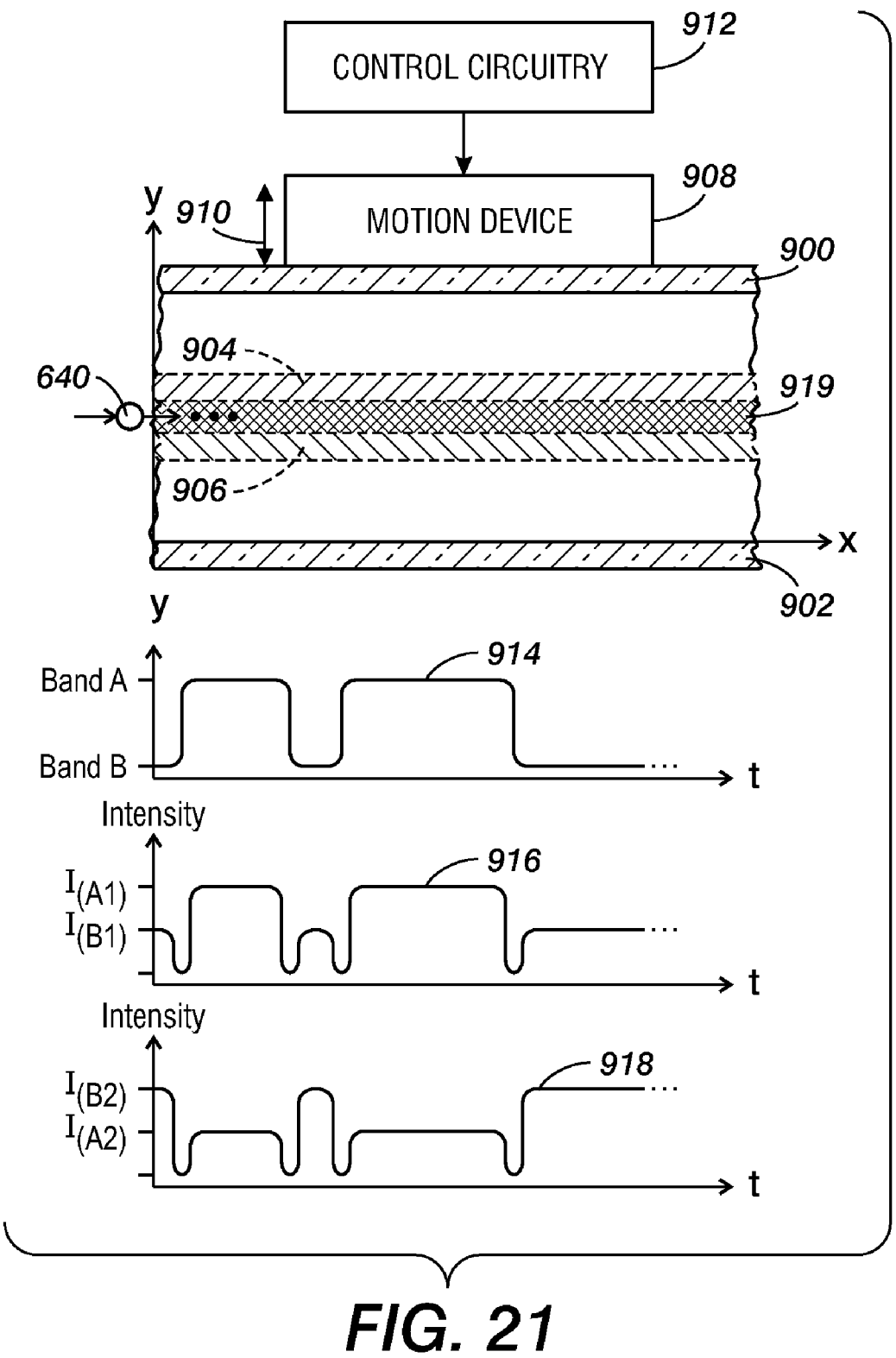
FIG. 21 is a partially schematic cross-sectional view of another displacement control arrangement that can be included in an encoding component as in FIG. 2, together with a graph showing displacement as a function of time and graphs showing intensity of emanating light as a function of time for exemplary types of objects.

FIG. 20 illustrates, on the other hand, how relatively simple time-varying signals could be produced using more complicated techniques. In general, such techniques assume that geometry of a channel directs flow of object 640 in a defined manner such as periodic, chirped, or random, past a sequence of filter elements. This allows redirection of particle flow past a simpler filter assembly geometry, and may be advantageous in cases where it is easier to redirect particle flow to produce a desired time-variation of emanating light than it would be to produce a filter assembly to produce the same time variation; for example, it might be easier to change channel wall shapes than to produce a desired filter assembly. In other cases, on the other hand, it might be advantageous to obtain more abrupt or rapid signal transitions with a well-defined filter assembly. In addition to the techniques described below, which involve shaping or moving walls, an object's flow within a channel could also be redirected by other techniques; an electrically charged object such as a particle, for example, could be redirected by electrical field variations. In general, however, the Reynolds number in typical microfluidic and nanofluidic implementations are so small that laminar flow conditions are, as a practical matter, always present.

In the example in FIG. 20, wall-like parts 880 and 882 are parallel but each of them is shaped like a sinusoidal wave, resulting in a sinusoidal flow pattern in the channel between them. Filter elements 884 and 886 are homogeneous of two different colors, illustratively labeled "A" and "B". As object 640 follows sinusoidal path 888, it moves back and forth between elements 884 and 886, passing through a small gap between them twice during each period. Curves 890 and 892 illustrate exemplary time-varying signals that could result from an object traveling along path 888. Curve 890 illustrates an example of an object of a type with a spectrum similar to color A but different from color B, while curve 862 illustrates an example of an object of a type with a spectrum similar to color B and different from color A. As a result, the curves are somewhat complementary, although each curve goes to approximately 0 while path 888 is crossing stripe 894 of blocking material between elements 884 and 886. Blocking material could also be provided outside elements 884 and 886.

Wall-like parts 900 and 902 in FIG. 21 are substantially straight and parallel, with filter elements 904 and 906 between them, similar to elements 884 and 886 in FIG. 21. Motion device 908 produces relative movement between the path of object 640 and stripe-like elements 904 and 906, as indicated by bi-directional arrow 910. Control circuitry 912 provides signals to control operation of motion device 908, which need not be periodic, but could take any appropriate pattern, resulting in arbitrary time-varying signals with features indicating different types of objects. An alternative would be to move elements 904 and 906; more generally, any combination of relative movements between walls 900 and 902 on the one hand and elements 904 and 906 on the other could produce movement as indicated by bi-directional arrow 910. Furthermore, additional variations could be produced by changing fluid flow within the channel so that the speed or other displacement of object 640 changes as a function of time relative to the other movements. Motion device 908 could be set up to produce variations in response to trigger signals indicating incoming objects.

Curve 914 illustrates movement of object 640 between element 904, labeled "Band A", and element 906, labeled "Band B". As illustrated, object 640 spends different lengths of time in each region and can spend a random amount of time in each region, resulting in a random excitation pattern. Curves 916 and 918 illustrate exemplary time-varying signals that could be produced by the technique of FIG. 21. One type of object has a spectrum more similar to color A of element 904, as illustrated by curve 916, while the other has a spectrum more similar to color B of element 906, as illustrated by curve 918. As each object travels between elements 904 and 906, it passes over stripe 919 of blocking material between them, resulting in a brief interruption of the emanating light, so that each curve goes briefly to 0. In curve 916, the intensity along element 904 is I(A1), while the intensity along element 906 is I(B1), a lower value linearly. Conversely, curve 918 illustrates that the intensity is higher along element 906, at intensity I(B2), and lower along element 904, at intensity I(A2). The two curves are, in general, complementary, except for times when they are passing stripe 919 between element 904 and 906; object 640 can be moved instantaneously between Band A and Band B, moving very quickly across stripe 919, so that the time in which it is passing stripe 919 are very brief.

Figure 22:
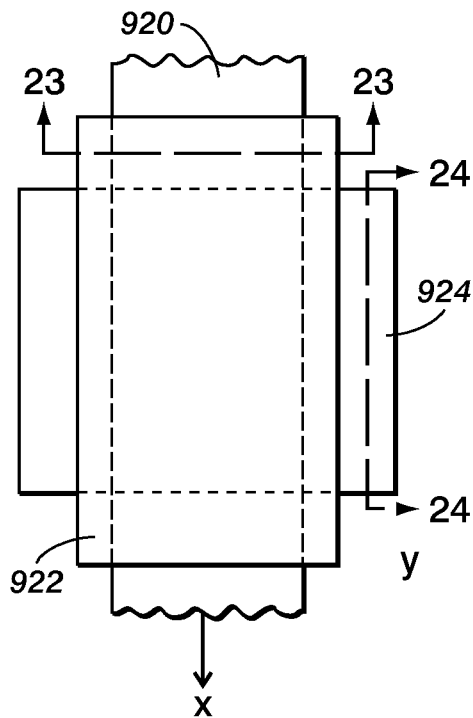
FIG. 22 is a top view of an implementation of a fluidic channel with an encoding arrangement that can be included in an implementation with features as in FIG. 1.
Figure 23:
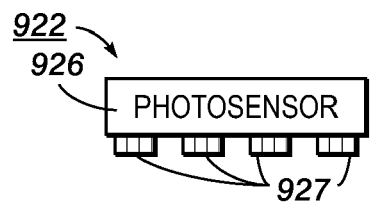
FIG. 23 is a cross-sectional view of a component in FIG. 22, taken along the line 23-23.
Figure 24:
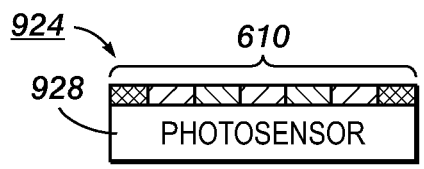
FIG. 24 is a cross-sectional view of another component in FIG. 22, taken along the line 24-24.

FIGS. 22-24 illustrate implementations of filter arrangements in which filter assemblies are on opposite sides of channel 920. In the illustrated implementation, detector 922, shown on the near side of channel 920, includes one filter assembly, while detector 924, on the far side of channel 920, includes another filter assembly. Although each detector could be implemented in a wide variety of different ways, to obtain information about emanating light and objects from which light emanates, FIGS. 23 and 24 illustrate an example in which detector 922 includes a periodic filter assembly with periodicity in a direction transverse to channel 920, labeled the y-direction, and detector 924 includes a random two-color filter assembly with a longitudinal sequence in the x-direction, though other angles between the x- and y-directions might also be useful including, in some cases, implementations in which they are parallel. In the illustrated case, sensing results from detector 922 include signals modulated in the y-direction, while sensing results from detector 924 indicate signals modulated in the x-direction. The two modulations can be used to obtain information about an object from which light is emanating.

As shown in FIG. 23, detector 922 can be implemented with photosensor 926 on a photosensitive surface of which are filters 927, periodic in the y-direction; each of filters 927 is illustratively a red band pass filter, but they could instead be any other color or closed filters or intermediate intensity gray scale filters, and could be implemented with absorption, reflection, or interference-based filtering techniques as described above. Similarly, FIG. 24 shows an implementation of detector 924 in which photosensor 928 has filter assembly 610 (FIG. 9) on its photosensitive surface; photosensor 928 could also have a periodic filter superimposed on filter assembly 610 or in place of filter assembly 610, in which case it might include green filters (not shown).

A wide variety of other arrangements similar to FIGS. 22-24 would be possible, including, for example, another type of template layer on one side of channel 920 to provide a desired signal as described in co-pending U.S. patent application Ser. No. 12/022,485 entitled "Obtaining Information from Time Variation of Sensing Results", incorporated herein by reference in its entirety, and a periodic mask layer to provide a periodic signal on the other side of channel 920; in this implementation, the periodic signal could be constantly analyzed to obtain values indicating displacement of an object currently flowing through channel 920, which could be used to determine an appropriate time scale for correlation with the template signal similar to techniques described. In another possible variation, emanating light from fluorescence could be photosensed on one side of channel 920 and emanating light due to scattering, for example, could be photosensed on the other side.

Some of the exemplary implementations described below involve filter assemblies that combine periodic signals additively with template signals from filter sequences similar to some of those described above. The resulting time-varying signal emerges from the filter assembly with two different spatially varying patterns imposed on it. To produce such a signal, for example, a radial sequence or "stack" of filters similar to that shown in FIG. 4 could be used. Within a stack of filters, for example, one layer could be a template layer with an appropriate pattern to produce the template signal, while another layer could be a periodic layer with an appropriate pattern to produce the periodic signal; each of the template layer and periodic layer could have rectangles or other closed polygons of zero opacity surrounded by regions with opacity 0.5.

Figure 25:
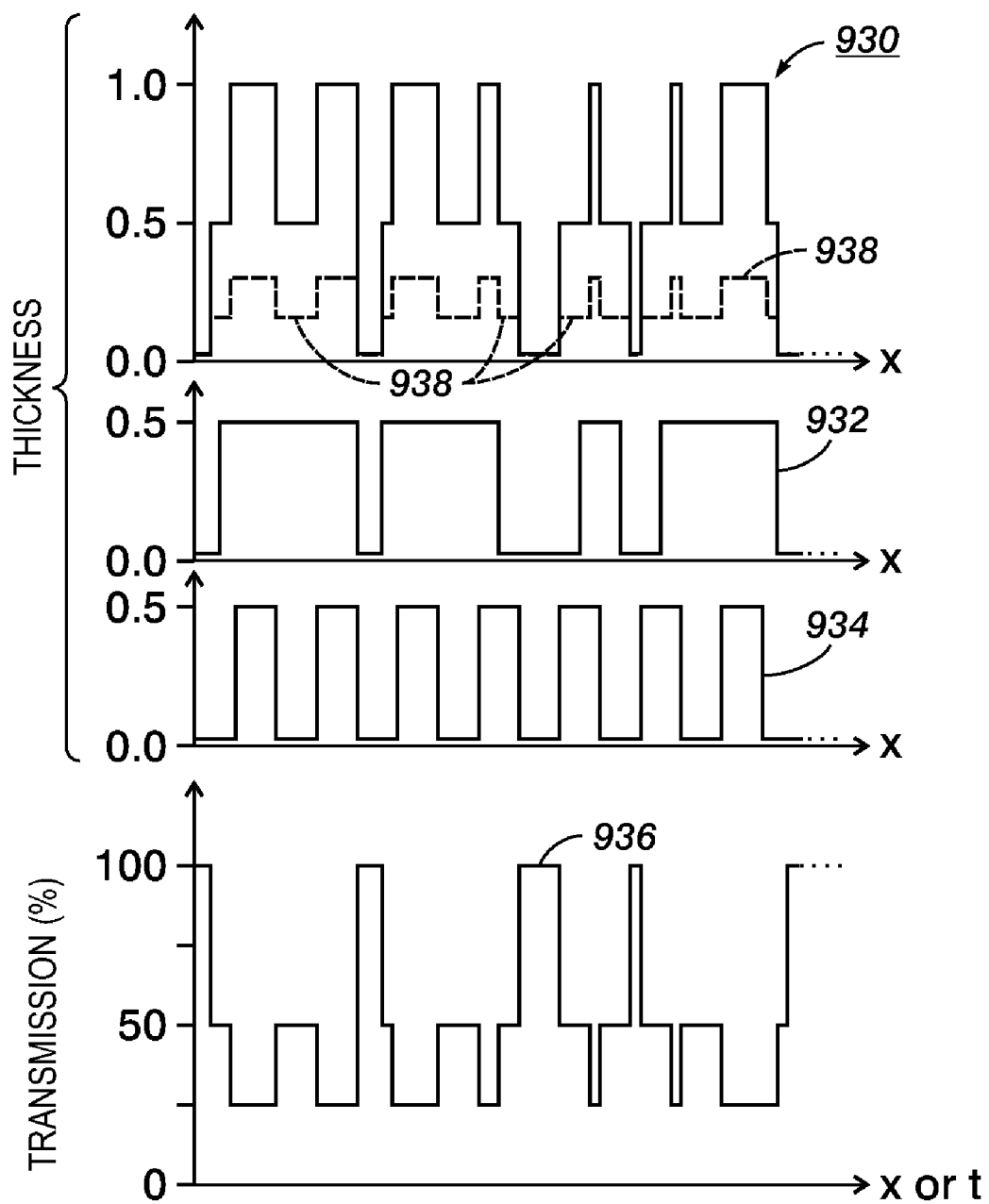
FIG. 25 includes a set of graphs showing cross-sectional thickness as a function of position in an x-direction for filters and showing transmission as a function of position in the x-direction or as a function of time t for one of the filters.
Figure 26:
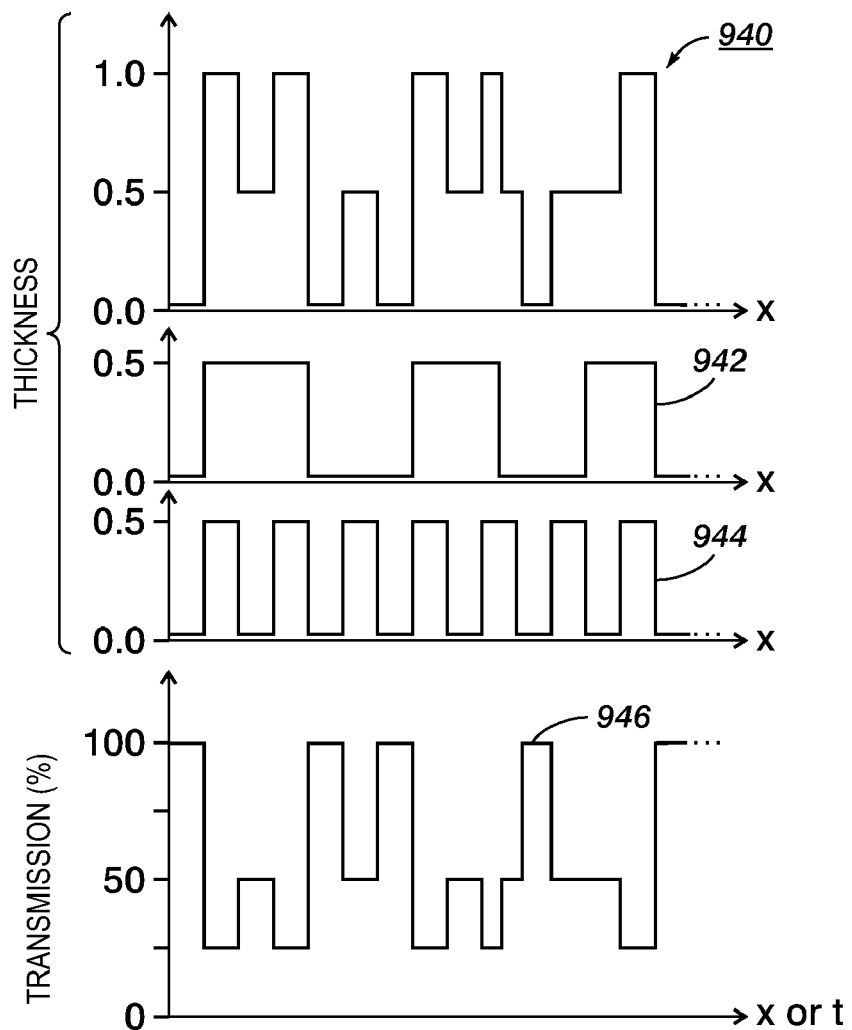
FIG. 26 includes a set of graphs showing cross-sectional thickness as a function of position in an x-direction for other filters and showing transmission as a function of position in the x-direction or as a function of time t for one of the filters.

FIGS. 25 and 26 illustrate an alternative approach that can be used with reflective gray scale filters, producing a single filter assembly equivalent to a desired radial sequence or stack of filters. To obtain filters as in FIGS. 25 and 26, thickness definitions of two filter layers can be overlaid using software tools and the thicknesses of overlapping regions can be added, resulting in regions with thicknesses of 0, 0.5, and 1 in the example given above; the two filter layers could both be oriented with variation in the same direction as in FIGS. 25 and 26, similar to the techniques of FIGS. 9 and 13, or could be oriented with variation in different directions, e.g. orthogonal to each other. For implementations in which layer thickness does not appropriately define or determine the desired equivalent filters structure or its optical variation, the techniques in FIGS. 25 and 26 could be modified to first overlay optical feature definitions of the filters in which regions have defined optical feature values that determine the desired variation, thus obtaining an optical feature definition of the desired equivalent filter; the optical feature definition could then be converted to a layout-type description of the equivalent filter in which each region has a defined optical thickness or other characteristic that can be produced to provide the region's value for the optical feature.

The techniques of FIG. 25-26 take advantage of the fact that, in general, superpositions of filters are commutative, in the sense that the resulting transmission or reflection function is the same regardless of the order in which filters are superimposed. There are, of course, exceptions, such as where interference effects can occur if filters are in a specific order, or where alignment or other relationship of filter features can result in loss of different information depending on the order of the filters.

If the equivalent filter definition is a thickness definition to produce a purely transmissive/reflective filter with no color variation, and if partial etching can be performed, an equivalent filter that approximates the equivalent filter definition can be constructed by first depositing a highly reflective material, such as chromium, over the entire filter assembly, and by then partially etching the reflective material away in regions with thickness 0 or 0.5 to an appropriate extent, leaving a thin, partially transmitting layer, after which the remaining reflective material can be etched away in regions with thickness of 0. Where partial etching is unreliable, other techniques may be used, such as by techniques that deposit a first patterned layer of thickness 0.5 with any suitable patterning technique, then depositing over it a second patterned layer of thickness 0.5 that is patterned without etching, such as with liftoff or other patterning techniques that do not require etching. Furthermore, similar techniques might be applied to produce layered filter structures that include DBRs of varying transmission/reflectivity and/or cavities of varying optical thickness, such as those described above in relation to FIGS. 16-18; variation in cavity thickness could result from any appropriate combination of thickness variation and refractive index variation, produced with any appropriate techniques.

Filter 930 in FIG. 25 is equivalent to the combination of a random filter and a periodic filter, superimposed one on the other. Curve 932 shows the shape of the random filter, while curve 934 shows the shape of the periodic filter; as can be seen, the random and periodic filters both have only two thickness levels, either 0 or 0.5, but filter assembly 930 has three thickness levels, corresponding to 0, 0.5, and 1. Curve 936 shows a resulting transmission function. Emanating light passing through filter assembly 930 includes both displacement and position information about an object from which it emanates, and allows time-scaling techniques to extract that information, as described below.

The technique illustrated in FIG. 25 can be adjusted as suggested by dashed lines 938 within filter 930. In other words, total light output can be changed by scaling the amplitude of the thickness levels: rather than 0, 0.5, and 1, for example, thickness levels of 0, 0.2, and 0.4 could be used, allowing greater light transmission. It may be necessary, however, to make a tradeoff between greater light output, and therefore total signal intensity, on the one hand, and greater light modulation on the other—greater light modulation may facilitate calculation of displacement and position within a given observation region. The mask suggested by dashed lines 938 emphasizes total light output because it has reduced thickness and, conversely, increased transmission, with a thickness of 0 being equivalent to transmission of 1 and vice versa. The scaling suggested by dashed lines 938 may require great precision: the x-direction scale of features in assembly 930 may be as great as 10 µm, while a useful thickness may be as thin as 10 nm of chromium.

Similarly, filter assembly 940 in FIG. 26 is equivalent to the combination of a chirp filter represented by curve 942 and a periodic filter represented by curve 944. A combination of chirp and periodic filters can make it possible to more efficiently extract displacement and position information about objects that may have different speeds. Curve 946 shows a resulting transmission function, which allows information extraction.

A stack-equivalent filter assembly as in FIGS. 25 and 26 can in some cases have a smaller MFS than either of the simpler non-uniform filters. As mentioned above, loss of resolution can occur for light emanating from objects approximately as large as the MFS.

Figure 27:
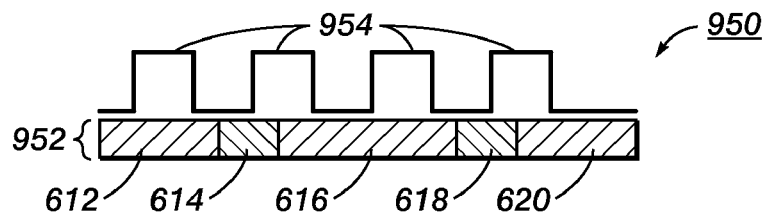
FIG. 27 is a schematic cross-sectional view of a filter assembly that includes two simpler filters.

FIG. 27 illustrates one way in which a longitudinal sequence of filters, such as a random band pass filter arrangement as described above in relation to FIGS. 9-12 can be combined with a reflective gray scale filter arrangement, illustratively a periodic gray scale filter. Filter arrangement 950 in FIG. 27 includes filter subassembly 952 with a longitudinal sequence similar to that described above in relation to FIGS. 9-12. On the upper surface of subassembly 952 is a periodic filter subassembly with regions 954, each having an intermediate transmission level such as 0.5. As a result, filter assembly 950 combines the technique of FIG. 25 with that of FIG. 12, providing distinguishable time-varying signals for emanating light of different colors, and also modulating the emanating light to allow time-scaling techniques as described below. In effect, the time-scaling operations can be performed in the same way for each emanating color's signal, and the different color signals can be used to distinguish types of objects after time scaling.

Figure 28:
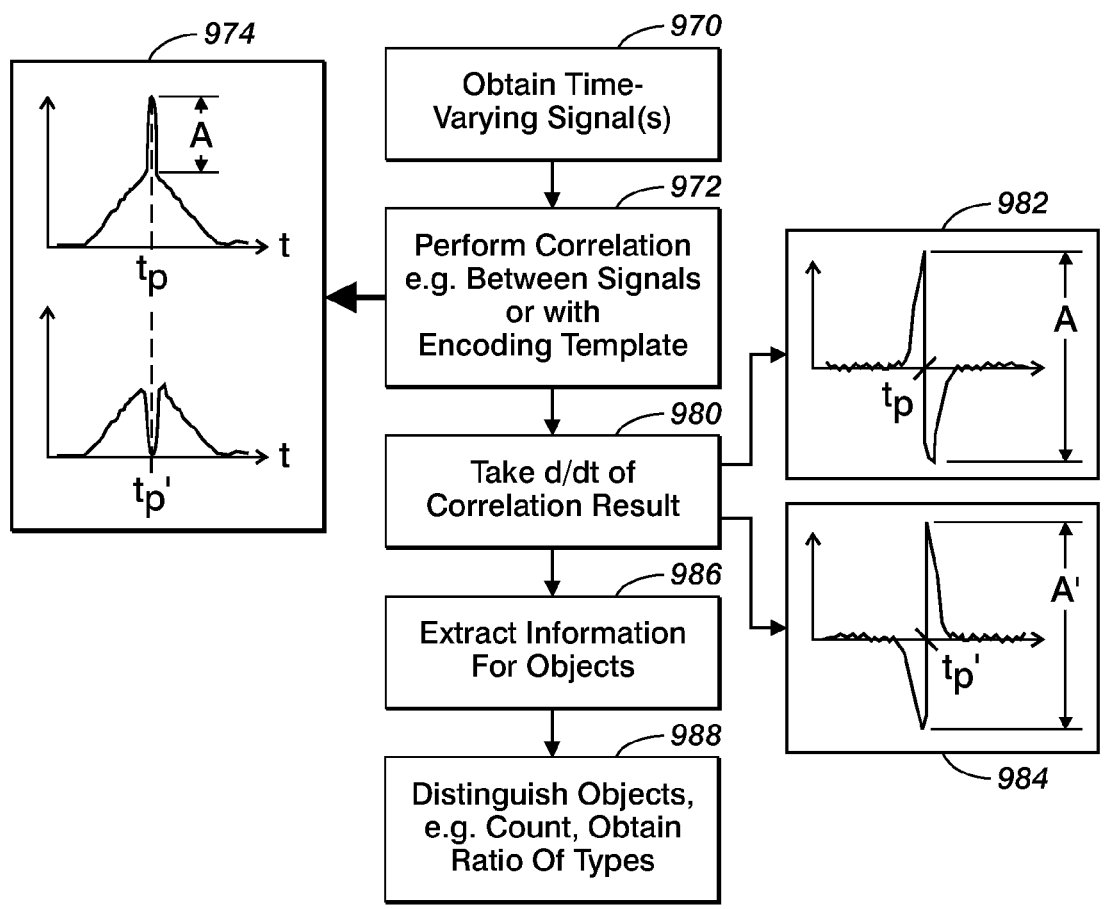
FIG. 28 is a flow chart with graphs illustrating an implementation in which information about objects is obtained from sensed time-varying signals.

The flow chart in FIG. 28 illustrates ways in which information about objects can be obtained and used by CPU 402 (FIG. 6); the technique of FIG. 28 illustratively extracts information such as a type, a position, or a spectral difference, and uses such information to distinguish objects. FIG. 28 also suggests ways in which routines 440, 442, and 444 (FIGS. 6 and 7) could be implemented. Although suitable for CPU 402, operations in FIG. 28 could be implemented with a wide variety of different types of circuitry with or without a CPU. Furthermore, although described in terms of time-varying signals from photosensors, the technique of FIG. 28 could be applied to any time-varying sensed signals, including, for example, capacitively sensed signals from charged particles with encoded information due to shapes, sizes, and positions of electrodes.

The operation in box 970 obtains one or more encoded time-varying signals from a photosensor arrangement as one or more objects travel along respective paths past a filter arrangement. The technique could be implemented with a single photosensor along the paths, but it might also be possible to implement with two photosensors on opposite sides of the paths or with other photosensor arrangements. The objects can, for example, travel through a channel as described above in relation to FIGS. 8-12 and 19-21 and the time-varying signals can be encoded in any of a wide variety of ways using filter arrangements, including one or more of those described above, with or without displacement control and/or spatially modulated excitation; excitation techniques that could be used are described in co-pending U.S. patent application Ser. No. 12/023,436 entitled "Producing Time Variation in Emanating Light", also incorporated herein by reference in its entirety. For example, if one of the filter arrangements is at least partially non-periodic or if displacement control or excitation is at least partially non-periodic, a respective template of the resulting non-periodic pattern for each of a number of types of objects can be used to perform a correlation operation; in other implementations, two differently encoded time-varying signals can be obtained in box 970 and correlated with each other. Note, however, that two types could be distinguished based on a single template, especially if their time-varying signals are sufficiently complementary that one results in correlation and the other in anti-correlation with the template.

The operation in box 970 can include providing any appropriate control signals to other components of the system, including signals to read out sensing results of photosensors. The control signals could be implemented as in routines 440 and 442 (FIG. 6), with CPU 402 providing signals through device I/O 420 to one or more of devices 422 through 424. For example, fluid flow speed could be adjusted and channel wall movement could be controlled as described above in relation to FIG. 21. In order to obtain the time-varying signals, CPU 402 could provide signals through IC I/O 410 to obtain photosensed quantities from ICs 412 through 414.

The operation in box 972 performs a correlation or other comparing operation on one or more time-varying signals from box 970, such as comparing two encoded signals with each other or comparing one encoded signal with a respective template of a non-periodic encoding pattern for each distinguishable type of object. As used herein, the term "correlation operation" encompasses any of a variety of mathematical operations that can be performed on a pair of time-varying functions, with or without scaling, and that obtains a similarity measure as a function of time-alignment. This correlation operation can be implemented, for example, as described in co-pending U.S. patent application Ser. No. 11/698,338, entitled "Method and System for Evaluation of Signals Received from Spatially Modulated Excitation and Emission to Accurately Determine Particle Positions and Distances", incorporated herein by reference in its entirety. Additional correlation and other comparison techniques that could be used are described in co-pending U.S. patent application Ser. No. 12/022,485 entitled "Obtaining Information from Time Variation of Sensing Results", also incorporated herein by reference in its entirety.

A correlation operation in box 972 can produce correlation results for each pair of waveforms that is compared. For example, if box 972 compares an encoded time-varying signal from box 970 with each of N templates for N types of objects, N correlation results are produced.

The graphed curves in box 974 illustrate two types of correlation results: The upper curve illustrates a correlation result where two time-varying waveforms are correlated, i.e. highly similar at the time alignment designated $t_p$; the lower curve illustrates a correlation result where two time-varying waveforms are anti-correlated, i.e. highly dissimilar at the time alignment designated $t_p'$. In each case there is a peak, with the peak in the correlated case marked to show its amplitude A and with the anti-correlated case having an inverted peak of similar amplitude. If correlation is performed on a continuous basis, correlation results could similarly be continuously obtained for each template with which comparison is made, with each object's travel past the filter arrangement producing a peak, an inverted peak, or a feature in between the two for each template.

The operation in box 980 obtains a time-varying waveform that equals or approximates the time derivative d/dt of each correlation result from box 972. For the correlated case, a derivative waveform like the graphed curve in box 982 is obtained, with a positive peak followed by a negative peak, with a zero crossing at $t_p$, and with the contrast or differential quantity between the peaks again being the amplitude A. For the anti-correlated case, a derivative waveform like the graphed curve in box 984 is obtained, with a negative peak followed by a positive peak, with a zero crossing at $t_p'$, and with the contrast or differential quantity between the peaks being amplitude A', the amplitude of the inverted peak in the lower graph in box 974. The amplitudes obtained in this manner are, in general, free of offsets, allowing direct comparison to obtain spectral information.

The operation in box 986 uses derivative waveforms from box 980 to extract information for objects passing the photosensor. The extracted information could, for example, be a type based on whether an object resulted in correlation, anti-correlation, or neither with a given template; position based on the time at which a zero crossing occurs in correlation or anti-correlation; and spectral difference, e.g. a difference of emission, absorption, or scattering spectrum, based on the amplitude or contrast between positive and negative peaks from correlation and anti-correlation, respectively. Features of a derivative waveform could be found and measured using various techniques. The operation in box 988 can then be performed to distinguish objects using information extracted in box 986, such as by obtaining counts of different types of objects or ratios between such counts, or with other operations as described above in relation to FIG. 7.

The operations in boxes 972, 980, and 986 could be implemented, for example, as parts of one or both of routines 442 and 444 (FIG. 6). The operation in box 988 could be implemented as part of routine 444. In general, these operations could be implemented to handle signals from each object separately or to handle a signal received concurrently or in series from a number of objects, in which case minimum differences, such as in positions or speeds, may be necessary to allow separation of signals from different objects. Any appropriate combination of serial and parallel operations could be implemented in any appropriate circuitry. Data streams or other data structures defining waveforms such as templates could be stored and retrieved as needed by routines 442 and 444, such as in memory 408 (FIG. 6). Similarly, intermediate and final results of operations in boxes 972, 980, 986, and 988 could similarly be stored and retrieved as needed.

Comparison techniques other than correlation could be employed, but correlation techniques can be advantageous because they are typically not sensitive to noise, such as an AC power frequency. For example, preliminary smoothing or other preprocessing of waveforms is typically unnecessary for correlation, and available techniques for computing correlations can produce useful results even with S/N ratios significantly less than 1.0. It is, however, necessary to satisfy minimum sampling requirements if waveforms are digitized for correlation; in accordance with the Nyquist frequency, each waveform should be sampled at least twice during the time duration of its minimum feature size.

Some techniques as described above have been successfully applied to simulated time-varying waveforms. In particular, time scaling techniques have been found to improve S/N ratio of a simulated observed signal that contains both an encoding based on a template and also additive noise, and where the observed signal has an unknown time scaling that occurs before it is observed; S/N ratio of 0.5 has been obtained and 0.1 appears achievable. These results could be obtained with particle speeds up to 0.5 m/sec and higher speeds up to a few m/sec appear to be feasible, with particles having effective sizes down to 0.6 µm, and with particle separations down to a given implementation's MFS. A demonstration included counting CD4 in a whole blood sample; single tag detection was shown to be feasible.

Where a simulated observed signal includes or is accompanied by a simulated concurrent periodically modulated signal, time scaling of a template waveform based on a scaling factor from the periodically modulated signal has successfully produced matching correlation results, indicating correlation or anti-correlation as appropriate and making spectral information available, in effect allowing concurrent detection of multiple colors with a single detector such as a large-area photosensor. Because an object receives different excitations at almost the same time and location (due, for example, to interdigitated or otherwise patchworked or patterned excitations), differences in absorption and excitation spectra can be measured with very high precision; similarly, because different spectral subranges of an object's emission spectra are measured at almost the same time and location (due, for example, to interdigitated, or otherwise patchworked or patterned filter arrangements), differences in emission spectra can be measured with very high precision; therefore, with one or both of patterned excitation and patterned filtering, many types of errors cancel out, including time-dependent factors such as bleaching, intermixing, diffusion and also errors induced by excitation differences such as temperature gradients and optical misalignments. Particle position can be precisely determined from fine structure of correlation results. As noted above, simulation results show that spatial resolution of less than 1.0 µm is possible, and single fluorescence markers can be detected, making detection possible with smaller amounts of consumables such as markers. The techniques appear appropriate for native fluorescence, allowing agent-less detection.

Some of the implementations described above in relation to FIGS. 1-28 are examples of a method of using a filter arrangement. While an object travels along a path past the filter arrangement and emanates light within an application's range of photon energies, the method transmits/reflects at least some of the emanating light through the filter arrangement. In doing so, the method includes at least one of the following two: First, while the object is in each of two or more segments of the path, the method transmits/reflects respective portions of the emanating light through respective positions of a filter assembly within the filter arrangement; each of the respective positions has a respective transmission function, and the transmission functions of at least two of the positions are sufficiently different that time variation occurs in the emanating light between at least two of the segments. Second, while the object is in each of a series of segments of the path, the method transmits/reflects a respective portion of the emanating light through a filter component within the filter arrangement, and the filter component has a combined transmission function in which a set of simpler transmission functions is superimposed; the set of transmission functions is superimposed such that time variation occurs in the emanating light in accordance with superposition of first and second simpler non-uniform transmission functions in the set.

In specific implementations, the method can do both, i.e. it transmits/reflects respective portions of the emanating light through respective positions of a filter assembly and also transmits/reflects a respective portion of the emanating light through a filter component. The filter assembly can include first and second filter elements that include first and second respective positions, and each of the first and second filter elements can have a respective transmission function that is approximately uniform for light from its respective segment of the path. For example, the transmission functions of the first and second filter elements can be spectrally different, and the method can encode spectral information in time variation of the emanating light. Also, the transmission functions can be different in transmitted/reflected intensity, and the method can encode intensity information in time variation of the emanating light. More generally, the method can encode information about the object in time variation of the emanating light, such as information indicating the type of the object.

In further specific implementations, each of the segments of the path can be at least approximately as large as the object's size. The combined transmission function can have a minimum feature size (MFS) at least approximately as large as the object's sizes. The series of segments in which the method transmits/reflects emanating light through the filter component can be substantially continuous. Similarly, the segments from which emanating light is transmitted/reflected through respective positions of the filter assembly can be segments within a sequence in part of the object's path. The method can cause the object to travel along the path with non-uniform displacement, such as by changing its displacement rate or its displacement direction. The object can be, for example, a biological cell or virus, and the application can be flow cytometry.

The simpler non-uniform transmission functions that are superimposed can include at least one that is non-periodic. Examples of simpler transmission functions can include, in addition to periodic functions, random and chirped functions.

Some of the implementations described above in relation to FIGS. 1-28 are examples of apparatus that includes a fluidic structure with a channel through which objects can travel along respective paths during operation and an encoding component with a filter arrangement that can receive light emanating from objects in the channel. In response to input light emanating from an object, the filter arrangement provides output light. The filter arrangement includes at least one of the following two: First, a filter assembly with a set of positions, each having a respective transmission function; a sequence of segments of an object's path including at least two segments from which respective positions in the set receive emanating light, and the transmission functions of the positions are sufficiently different from each other that time variation occurs in the output light while the object travels through the sequence of segments. Second, a filter component that receives input light from a segment of an object's path and has a combined transmission function in which a set of two or more simpler transmission functions are superimposed; the set includes first and second simpler non-uniform transmission functions, and the set is superimposed such that time variation occurs in the output light in accordance with superposition of the first and second simpler non-uniform transmission functions while the object travels through the segment.

In specific implementations, the apparatus can encode information about the object in time variation of the output light. The apparatus can also include a photosensing component that photosenses the time-varying output light and provides sensing results, such as with electrical signals. The apparatus can also include a processing component that responds to the sensing results, performing operations to obtain data indicating information encoded in the output light. The processing component can be programmed, for example, to perform a comparing operation to obtain comparison results between time-varying waveforms, at least one of which is from the sensing results, and can use the comparison results to obtain data indicating at least one spectral difference between the time-varying waveforms; the comparing operation can be correlation, and the time-varying waveforms can include a sensed time-varying waveform and a template time-varying waveform.

In specific implementations, the filter arrangement can include one or more of many different filter components, such as an absorption filter; an interference-based filter; a light-transmissive and/or light-reflective filter; a longitudinal sequence of filters that vary in a periodic, random, or chirped pattern; filter elements of two or more colors; filter elements of two or more gray levels; overlapping filter elements; a longitudinal sequence of filter elements that includes binary, gray level, and color filter elements; two or more lengthwise extending filter elements; a radial sequence of filter elements; two orthogonally striped filter assemblies; filter assemblies on opposite sides of a fluidic channel; and a stack-equivalent filter. The filter component can include the filter assembly, which can have one of the first and second simpler non-uniform transmission functions. At least one of the simpler non-uniform transmission functions can be a periodic, random, or chirp function of position.

In specific implementations, the apparatus can be a flow cytometer, with the objects being, for example, biological cells or viruses. In other implementations, the apparatus can be a scanning device.

Some of the implementations described above in relation to FIGS. 1-28 are examples of a method that transmits/reflects light emanating from objects through a filter arrangement while each object travels along a respective path past the filter arrangement. The method can transmit/reflect at least some of the object's emanating light through a longitudinal sequence of filter elements within the filter arrangement, while the object travels through a segment of its path. The longitudinal sequence includes a first subset of filter elements that have approximately a first transmission function and a second subset that have approximately a second function, with the first and second transmission functions being sufficiently spectrally different from each other that time variation occurs in the emanating light while the object travels through the segment.

In specific implementations, the time variation encodes spectral information about the object, and the method can photosense the emanating light to obtain photosensing results, then use the photosensing results to obtain data indicating the encoded spectral information. The photosensing results can indicate sensed time-varying waveforms, and the method can perform a comparing operation on a set of time-varying waveforms to obtain comparison results, with at least one of the time-varying waveforms being a sensed time-varying waveform; the method can use the comparison results to obtain data indicating at least one spectral difference between the time-varying waveforms.

In further specific implementations, where objects have different respective emanation spectra, the method can detect a difference between the spectra. The longitudinal sequence can be a sequence of spatially patterned filter elements that includes at least one spatially patterned color filter element and at least one spatially patterned non-color filter element such as a black and white or gray level filter element. More generally, a sequence of patterned filter elements can include patterns sufficiently different that different information items are concurrently encoded in the emanating light without loss of information.

Some of the implementations described above in relation to FIGS. 1-28 are examples of a method that transmits-reflects light from objects through a filter arrangement while the objects travel past the filter arrangement. The method transmits-reflects at least some of an object's emanating light through a filter component within the filter arrangement while the object travels through a segment of its path. The filter component has a combined transmission function in which a set of simpler transmission functions is superimposed. The set includes first and second simpler non-uniform transmission functions and is superimposed such that time variation occurs in the object's emanating light in accordance with superposition of the first and second simpler non-uniform transmission functions while the object travels through the segment.

In specific implementations, at least one of the first and second simpler non-uniform transmission functions is a spectrally-dependent function that transmits more than one color as a function of position. The first non-uniform transmission function can be a non-periodic spectrally-dependent transmission function and the second can be a period transmission function. At least one of the first and second non-uniform transmission functions can be a spectrally-independent transmission function that transmits black and white and/or gray scales. At least one of the simpler non-uniform transmission functions can be periodic, random, or chirped. As above, the time variation can encode information, and photosensing results can be used to obtain data indicating the encoded information.

Implementations as described above in relation to FIGS. 1-28 could be advantageously applied in a wide variety of sensing applications, possibly including, for example, fluorescence- or impedance-based flow cytometry or other biodetector applications that seek a signature of a particle of unknown velocity; such biodetectors often use microfluidic channels with inhomogeneous flow profiles, causing variation in particle velocity. The techniques can be used to count or obtain ratios between fluorescing objects of different types, such as different types of tagged cells, particles, tagged DNA, and so forth. In such an application, calibration can be performed using known objects, e.g., tagged beads, with known velocities to obtain template waveforms that include deviations caused by fabrication tolerances but can then be compared with sensed waveforms to obtain information about unknown objects. To improve S/N, known and sensed waveforms can be correlated, such as after time scaling of each known waveform. If a sensed waveform includes or is accompanied by periodic modulation, a periodicity value such as a frequency can be used to obtain a scaling factor for time scaling before correlation, allowing more rapid correlation than if a brute force technique is used to find a satisfactory time scaling.

Implementations described above may be advantageous in biodetector applications that require compact, low-cost components without critical optics and with high sensing efficiency. Such applications might include point-of-care flow cytometry (such as with an integrated flow cytometer), DNA analysis, proteomics, and so forth.

Implementations described above could successfully detect native fluorescence differences between biological materials. Most biological cells are composed of only a few basic building blocks and, therefore, exhibit similar native fluorescence spectra. Interdigitated or otherwise patch-worked or patterned filter arrangements like those above are particular suitable for differentiation of objects based on their native fluorescence signals because the techniques are sensitive enough to detect the native fluorescence from a single cell and allow direct measurement of distinguishing features such as intensity ratios in emission spectra. In addition, implementations of the techniques can combine advantages of excitation and emission spectroscopy in a rugged and compact system.

Also, implementations described above could be applied in scanning of bio-chips or documents where objects have different emanation spectra, and so forth. The techniques may also be applicable in various low S/N ratio systems in which a known signal is bounced off an object traveling at an unknown velocity, such as where object velocity is on the order of signal propagation velocity, as in SONAR. The techniques may be especially advantageous where precise information about position, speed, or type of objects is sought.

Exemplary implementations described above employ photosensors or impedance-based sensors with specific features, but a wide variety of sensors could be used to obtain sensing results indicating values of various parameters other than emanating light intensity, parameters that can have time variation that indicates information about objects. Similarly, implementations described above involve sensing information about objects that are moving in fluidic channels or that are moving relative to a sensor such as in scanning, but various other types of fluidic implementations or other implementations in which objects move in various other ways could be sensed to obtain sensing results suitable for techniques described above. For example, information could be obtained from native fluorescence of particles in an air stream. Also, an excitation pattern could be scanned across a glass slide with immobilized analyte particles such as tagged cells or DNA spots, to obtain emanating fluorescent light.

Components of exemplary implementations as described above could have various shapes, dimensions, or other numerical or qualitative characteristics other than those illustrated and described above. Similarly, although the exemplary implementations generally involve sensing from a single fluidic channel, implementations could readily include multiple parallel channels, allowing parallel sensing and readout and larger scale sensing.

Some of the above exemplary implementations involve specific types of fluidic components, filter components, light source components, displacement control components, sensors, and so forth, but the invention could be implemented with a wide variety of other types of components. For example, some implementations use specific types of spatial modulation based on one or more of an excitation pattern, a filter assembly, and/or displacement control, but various other types of spatial modulation could be used, including any appropriate combination of color, gray level, and black and white patterning and including other patterning techniques such as patterned sensing; for example, in a fluidic implementation, a filter assembly or a patterned photosensor could be printed or otherwise produced on an inward wall or other boundary of a channel or in another appropriate location. Also, some exemplary implementations use specific types of processing, such as digital signals obtained after converting sensed analog values. In general, however, the invention could be implemented with any suitable signal processing techniques, including any appropriate combination of analog and digital processing; either or both of two compared waveforms could be obtained in analog or digital form, and any combination of time scaling could be performed before comparison. Further, some exemplary implementations use large area photosensors, but various ICs with photosensing arrays might be used.

Some of the above exemplary implementations involve specific types of emanating light, e.g. fluorescence, and specific types of excitation and filtering suitable to fluorescent light, but these are merely exemplary. The invention could be implemented in relation to various other types of optical signals in various other ranges of photon energies or with any other appropriate sensed stimuli.

Some of the above exemplary implementations involve specific materials, such as in fluidic structures with light-transmissive components or in filtering arrangements with reflective material or light blocking material such as amorphous silicon, but the invention could be implemented with a wide variety of materials and with layered structures with various combinations of sublayers. Thicknesses of layers may vary across any suitable range.

The exemplary implementation in FIG. 6 employs a CPU, which could be a microprocessor or any other appropriate component. Furthermore, as noted above, operations could be performed digitally or with analog signals, and could be done either on the same IC as a photosensor array, on other components, or on a combination of the two, with any appropriate combination of software or hardware.

The above exemplary implementations generally involve use of encoding/sensing arrangements, sensors, photosensors, excitation arrangements, filter arrangements, displacement control arrangements, and so forth following particular operations, but different operations could be performed, the order of the operations could be modified, and additional operations could be added within the scope of the invention. For example, readout of sensed quantities from a sensor to obtain a sensed time-varying waveform could be performed serially or in parallel, and, with an array, could be performed cell-by-cell or in a streaming operation. Principal component analysis could be applied to specifically chosen intensity ratios in the emission spectrum in distinguishing cells or other objects, possibly allowing identification. Multiple photosensors along a channel could measure different intensity ratios in the emission spectrum, possibly allowing identification of objects based on either emission characteristics. Dyes that are very similar may be distinguishable if they reveal only slightly different emission spectra, and use of similar dyes could be advantageous in satisfying pH requirements within cytometers.

While the invention has been described in conjunction with specific exemplary implementations, it is evident to those skilled in the art that many alternatives, modifications, and variations will be apparent in light of the foregoing description. Accordingly, the invention is intended to embrace all other such alternatives, modifications, and variations that fall within the spirit and scope of the appended claims.

What is claimed is:

1. A method of using a filter arrangement, the method comprising:

while an object travels along a path past the filter arrangement and emanates light within an application's range of photon energies, transmitting/reflecting at least some of the emanating light through the filter arrangement;

the act of transmitting/reflecting at least some of the emanating light through the filter arrangement including at least one of:

while the object is in each of a substantially continuous series of two or more segments of the path, transmitting/reflecting respective portions of the emanating light through respective positions of a filter assembly within the filter arrangement; each of the respective positions having a respective transmission function within the range; two of the positions that are adjacent having respective transmission functions sufficiently different from each other that the difference causes time variation in the emanating light between the respective segments; and while the object is in each of a series of segments of the path, transmitting/reflecting a respective portion of the emanating light through a filter component within the filter arrangement; within the range, the filter component having a combined transmission function in which a set of two or more simpler transmission functions is superimposed; the set including first and second simpler non-uniform transmission functions, the set being superimposed such that time variation occurs in the emanating light in accordance with superposition of the first and second simpler non-uniform transmission functions.

2. The method of claim 1 in which the filter assembly includes first and second filter elements that include first and second ones of the respective positions, respectively; each of the first and second filter elements having a respective transmission function that is approximately uniform for light from the respective segment.

3. The method of claim 2 in which the transmission functions of the first and second filter elements are spectrally different; the act of transmitting/reflecting respective portions of the emanating light through respective positions including:
encoding spectral information in time variation of the emanating light.

4. The method of claim 2 in which the transmission functions of the first and second filter elements are different in transmitted/reflected intensity; the act of transmitting/reflecting respective portions of the emanating light through respective positions including:
encoding intensity information in time variation of the emanating light.

5. Apparatus comprising:
a fluidic structure that includes a channel through which objects can travel along respective paths during operation of the apparatus; and
an encoding component; the encoding component including a filter arrangement that can receive light emanating from objects in the channel; in response to input light that is within an application's range of photon energies and that is emanating from an object traveling through the channel past the filter arrangement, the filter arrangement providing output light; the filter arrangement including at least one of:
a filter assembly that includes a set of positions, each having a respective transmission function within the range; a substantially continuous series of segments of an object's path including at least two segments from which respective positions in the set receive light emanating from the object, two of the respective positions that are adjacent having respective transmission functions sufficiently different from each other that the difference causes time variation in the output light while the object travels through the respective segments; and
a filter component that receives input light from a segment of an object's path and that, within the range, has a combined transmission function in which a set of two or more simpler transmission functions is superimposed; the set including first and second simpler non-uniform transmission functions, the set being superimposed such that time variation occurs in the output light in accordance with superposition of the first and second simpler non-uniform transmission functions while the object travels through the segment.

6. The apparatus of claim 5 in which the filter arrangement includes at least one of:
an absorption filter;
an interference-based filter;
a light-transmissive and/or light-reflective filter;
a longitudinal sequence of filters that vary in a periodic, random, or chirped pattern;
filter elements of two or more colors;
filter elements of two or more gray levels;
overlapping filter elements;
a longitudinal sequence of filter elements that includes binary, gray level, and color filter elements;
two or more lengthwise extending filter elements;
a radial sequence of filter elements;
two orthogonally striped filter assemblies;
filter assemblies on opposite sides of a fluidic channel; and
a stack-equivalent filter.

7. A method comprising:
while objects travel along respective paths past a filter arrangement, transmitting/reflecting light emanating from the objects through the filter arrangement, the emanating light including photon energies within a range of photon energies; the act of transmitting/reflecting light through the filter arrangement including:
while an object travels through a segment of its respective path, transmitting/reflecting at least some of the object's emanating light through a longitudinal sequence of two or more filter elements within the filter arrangement; the longitudinal sequence including a first subset of one or more filter elements each having approximately a first transmission function within the range of photon energies and a second subset of one or more filter elements each having approximately a second transmission function within the range of photon energies, the first and second transmission functions being sufficiently spectrally different from each other that time variation occurs in the emanating light while the object travels through the segment.

8. The method of claim 7 in which the time variation encodes spectral information about the object, the method further comprising:
photosensing the emanating light to obtain sensing results; and
using the sensing results to obtain data indicating the encoded spectral information.

9. The method of claim 8 in which the sensing results indicate one or more sensed time-varying waveforms; the act of using the sensing results including:
performing a comparing operation on a set of time-varying waveforms to obtain comparison results, at least one of the set being a sensed time-varying waveform; and
using the comparison results to obtain data indicating at least one spectral difference between the time-varying waveforms in the set.

10. A method comprising:
while objects travel along respective paths past a filter arrangement, transmitting/reflecting light emanating from the objects through the filter arrangement, the emanating light including photon energies within a range of photon energies; the act of transmitting/reflecting light through the filter arrangement including:

while an object travels through a segment of its path, transmitting/reflecting at least some of the object's emanating light through a filter component within the filter arrangement; the filter component having a combined transmission function in which a set of two or more simpler transmission functions is superimposed; the set including first and second simpler non-uniform transmission functions, the set being superimposed such that time variation occurs in the object's emanating light in accordance with superposition of the first and second simpler non-uniform transmission functions while the object travels through the segment.

11. The method of claim 10 in which at least one of the first and second simpler non-uniform transmission functions is a spectrally-dependent transmission function that transmits more than one color as a function of position.

12. The method of claim 10 in which the first simpler non-uniform transmission function is a non-periodic spectrally-dependent transmission function; the second simpler non-uniform transmission function being a periodic transmission function.

13. The method of claim 10 in which at least one of the first and second simpler non-uniform transmission functions is a spectrally-independent transmission function that transmits black and white and/or gray scales.

14. The method of claim 10 in which at least one of the first and second simpler non-uniform transmission functions is a periodic, random, or chirp function of position along the segment.

15. A method of using a photosensor, the method comprising:

while a light-emanating object travels along a path past the photosensor, photosensing the object's emanating light to obtain sensing results; and using the sensing results to obtain information about the object;

the emanating tight having time variation indicating spectral information about the object's emission spectrum: the sensing results indicating one or more sensed time-varying waveforms; the act of using the sensing results comprising:

performing a comparing operation on a set of time-varying waveforms to obtain comparison results, at least one of the set being a sensed time-varying waveform; and using the comparison results to obtain data indicating the spectral information about the object;

the act of using the comparison results including at least one of:

performing an operation that obtains a time derivative of a waveform indicating comparison results;

performing an operation that obtains a derivative waveform with a positive peak followed by a negative peak;

performing an operation that obtains a derivative waveform with a negative peak followed by a positive peak;

performing an operation that obtains an amplitude of a peak in a waveform indicating comparison results;

performing an operation that obtains an amplitude between positive and negative peaks in a derivative waveform; and obtaining data indicating spectral difference.

16. A method of using filter arrangements, the method comprising:

while an object travels along a path past a filter arrangement and emanates light within an application's range of photon energies, transmitting/reflecting at least some of the emanating light through the filter arrangement; the act of transmitting/reflecting at least some of the emanating light through the filter arrangement including at least one of:

while the object travels through a segment of the path, transmitting/reflecting respective portions of the emanating light through a longitudinal sequence of two or more filter elements within the filter arrangement; the longitudinal sequence including a first subset of one or more filter elements each having approximately a first transmission function within the range of photon energies and a second subset of one or more filter elements each having approximately a second transmission function within the range of photon energies, the first and second transmission functions being sufficiently different from each other that time variation occurs in the emanating light in accordance with the longitudinal sequence; and while the object is in each of a series of segments of the path, transmitting/reflecting a respective portion of the emanating light through a filter component within the filter arrangement; within the range, the filter component having a combined transmission function in which a set of two or more simpler transmission functions are superimposed; the set including first and second simpler non-uniform transmission functions, the set being superimposed such that time variation occurs in the emanating light in accordance with superposition of the first and second simpler non-uniform transmission functions.

17. The method of claim 16 in which the act of transmitting/reflecting at least some of the emanating light through the filter arrangement includes both the act of transmitting/reflecting respective portions of the emanating light through a longitudinal sequence of two or more filter elements and also the act of transmitting/reflecting a respective portion of the emanating light through a filter component.

18. The method of claim 16 in which at least one of the simpler transmission functions is non-periodic.

19. Apparatus comprising:

a fluidic structure that includes a channel through which objects can travel along respective paths during operation of the apparatus; and an encoding component; the encoding component including a filter arrangement that can receive light emanating from objects in the channel; in response to input light that is within an application's range of photon energies and that is emanating from an object traveling through the channel past the filter arrangement, the filter arrangement providing output light; the filter arrangement including at least one of:

a longitudinal sequence of two or more filter elements; the longitudinal sequence including a first subset of one or more filter elements each having approximately a first transmission function within the range of photon energies and a second subset of one or more filter elements each having approximately a second transmission function within the range of photon energies, the first and second transmission functions being sufficiently different from each other that time variation occurs in the output light in accordance with the longitudinal sequence; and a filter component that receives input light from a segment of an object's path and that, within the range, has a combined transmission function in which a set of two or more simpler transmission functions is superimposed; the set including first and second simpler non-uniform transmission functions, the set being superimposed such that time variation occurs in the output light in accordance with superposition of the first and second simpler non-uniform transmission functions while the object travels through the segment.

20. The apparatus of claim 19 in which the filter component includes the longitudinal sequence, the longitudinal sequence having one of the first and second simpler non-uniform transmission functions.

21. The apparatus of claim 19, further comprising:
a photosensing component that photosenses the output light and provides sensing results; and
a processing component that, in response to the sensing results, performs operations to obtain data indicating information encoded in the output light.

22. The apparatus of claim 21 in which the sensing results indicate one or more sensed time-varying waveforms, the processing component being programmed to:
perform a comparing operation on a set of time-varying waveforms to obtain comparison results, at least one of the set being a sensed time-varying waveform; and
use the comparison results to obtain data indicating at least one spectral difference between the time-varying waveforms in the set.

23. The apparatus of claim 19 in which at least one of the simpler non-uniform transmission functions is a periodic, random, or chirp function of position.

24. The apparatus of claim 19 in which the objects are biological cells or viruses and the apparatus is a flow cytometer.

* * * * *